United States Patent [19]

Bihn

[11] Patent Number: 4,476,869
[45] Date of Patent: Oct. 16, 1984

[54] PACER ANALYZER

[75] Inventor: Daniel Bihn, Aptos, Calif.

[73] Assignee: Intermedics, Inc., Freeport, Tex.

[21] Appl. No.: 413,402

[22] Filed: Aug. 31, 1982

Related U.S. Application Data

[63] Continuation of Ser. No. 156,662, Jun. 5, 1980, abandoned.

[51] Int. Cl.³ .............................................. A61N 1/36
[52] U.S. Cl. ............................................ 128/419 PT
[58] Field of Search .................... 128/697, 419 PT

[56] References Cited

U.S. PATENT DOCUMENTS

| | | | |
|---|---|---|---|
| 3,426,748 | 2/1969 | Bowers | 128/419 PT |
| 3,757,790 | 9/1973 | Herrmann | 128/419 PT |
| 3,768,487 | 10/1973 | Ross | 128/419 PT |
| 3,885,552 | 5/1975 | Kennedy | 128/419 PT |
| 4,041,954 | 8/1977 | Ohara | 128/419 PT |
| 4,141,367 | 2/1979 | Ferreira | 128/419 PT |
| 4,172,459 | 10/1979 | Hepp | 128/419 PT |
| 4,250,884 | 2/1981 | Hartlaub et al. | 128/419 PT |
| 4,295,468 | 10/1981 | Bartelt | 128/419 PT |

OTHER PUBLICATIONS

Wiegand et al., "Medical Instrumentation," vol. 12, No. 3, May–Jun. 1978, pp. 180–183.

Bakema et al., "Medical & Biological Engineering & Computing", vol. 17, No. 5, Sep., 1979, pp. 667–670.

Primary Examiner—William E. Kamm
Attorney, Agent, or Firm—Willian Brinks Olds Hofer Gilson & Lione Ltd.

[57] ABSTRACT

An analyzer system is provided for checking the compatibility between a cardiac pacer and the stimulation requirements of the patient within which the pacer is to be implanted. Apparatus is provided which is convenient for use in an operating room environment, including a single rotary switch for varying the value of all selectable functions and providing both audio and visual feedback to the operator. Two interacting digital processing circuits provide a plurality of output waveforms suitable for use in testing the cardiac pacer and for pacing the patient. One digital processor circuit provides routine control of an analog system for generating waveform shapes and for monitoring response from the cardiac pacer or the electrode leads implanted in the patient. Another digital processor circuit accepts input from the operation selection keys and the rotary switch, executes a variety of operative routines, and varies operating parameters of the analog system such as amplitude, interval, and duration. To permit operation over a wide range of parameter values, various circuits and operating routines are provided for enhancing the measurements where an otherwise low sensitivity and resulting loss of precision would be obtained.

45 Claims, 18 Drawing Figures

FIG. 4
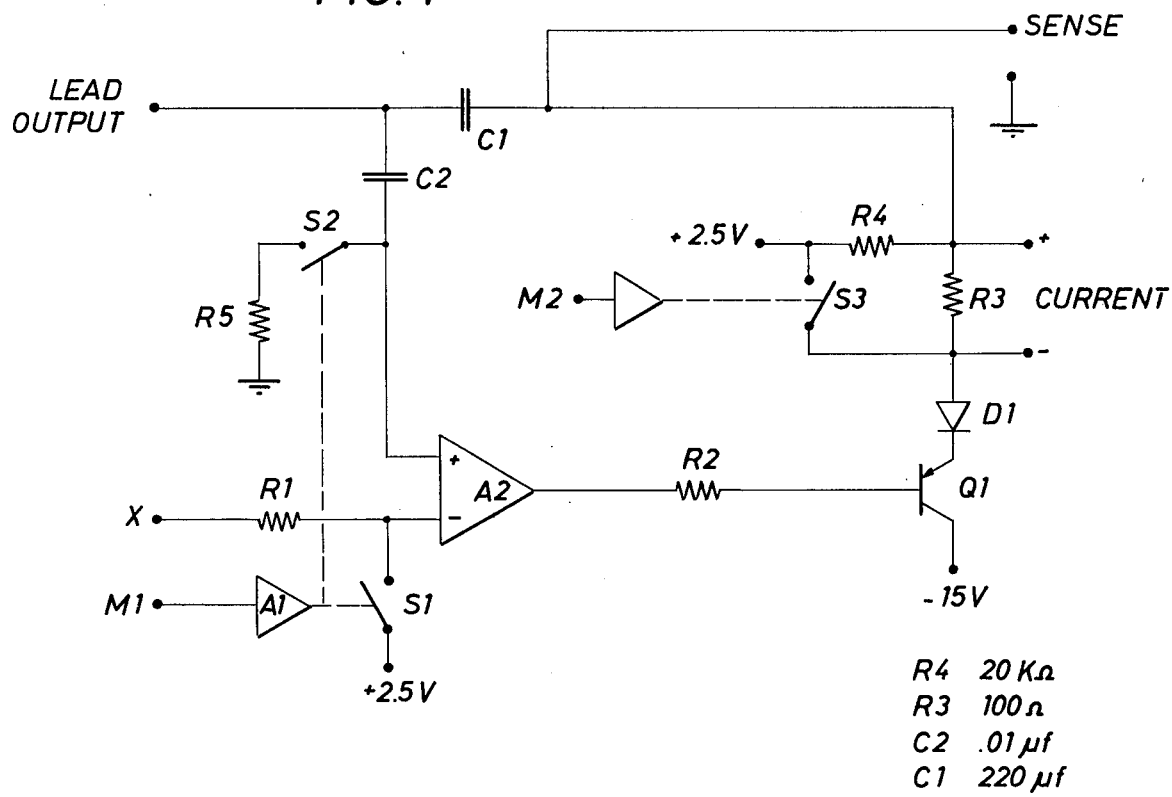
R4  20 KΩ
R3  100 Ω
C2  .01 μf
C1  220 μf
FIG. 4A
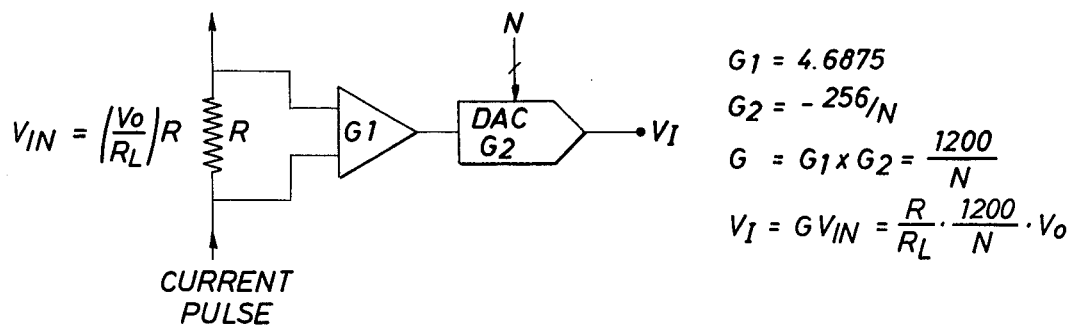
$V_{IN} = \left(\frac{V_o}{R_L}\right) R$
$G_1 = 4.6875$
$G_2 = -256/N$
$G = G_1 \times G_2 = \frac{1200}{N}$
$V_I = GV_{IN} = \frac{R}{R_L} \cdot \frac{1200}{N} \cdot V_o$
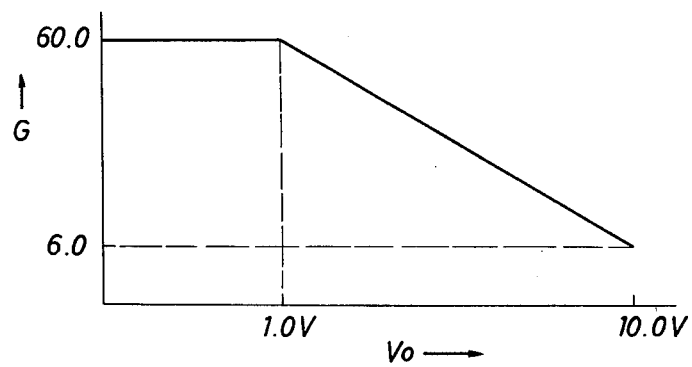
$G = 60$ FOR $V_o \leq 1.0 V$
$G = \frac{60}{V_o}$ FOR $V_o \geq 1.0 V$
FIG. 4B

FOR PULSE WIDTH ≤ T, SET GAIN = N AND CURRENT ∝ INTEGRAL / PULSE WIDTH.

FOR PULSE WIDTH ≥ T, SET GAIN(N) = CONSTANT/ PULSE WIDTH; CURRENT ∝ INTEGRAL

PACER ANALYZER

This application is a continuation of application Ser. No. 156,662, filed June 5, 1980, now abandoned.

BACKGROUND OF THE INVENTION

This invention relates to medical apparatus for electrically stimulating body functions and, more particularly, to apparatus for performing compatability checks between a stimulating device and the patient prior to implanting the device in the patient. In a particular embodiment, a pacer analyzer is provided for determining the electrical requirements of an electrode assembly implanted in a patient's heart, for determining the output available from a pacer which is about to be implanted in the patient, and for determining a measure of safety margin between the pacer's operating characteristics and the electrode stimulating requirements.

When it is determined that a cardiac pacer will assist in maintaining the cardiac output, a variety of implantable pacers exists to provide stimulating pulses. Many of the cardiac pacers are provided with a fixed set of operating parameters; other pacers provide for a limited adjustment in a few of the parameters. It is desirable to verify that the operating characteristics of such pacers are compatible with the patient within which the pacer is to be implanted. Still other pacers are programmable, having a variety of adjustable operating parameters. For these pacers, it is desirable to adjust the operating characteristics to match the particular patient prior to implanting the pacer.

In the course of implanting a pacer, an electrode is first inserted into the heart and the stimulating electrode tip lodged adjacent heart tissue in the ventricle and/or the atrium. The exact placement of the electrode tip and its electrical contact with the heart tissue determine the stimulating requirements for a given pacer output pulse. Thus, the compatibility between the pacer which is to be implanted and the electrodes lodged in the heart can only be determined at the time of implantation. It is very desirable to be able to measure various characteristics of the implanted electrodes and various output parameters of the pacer to obtain a check on the compatibility before actually implanting the pacer in the patient.

A typical prior art device for accomplishing this compatibility check is shown in U.S. Pat. No. 4,141,367, issued Feb. 27, 1979, to Med Telectronics, Ltd. The device depicted therein provides for obtaining measurements of external pacer characteristics, such as rate, pulse width, peak voltage, and trailing edge voltage. The pacer analyzer uses a simulated R-wave having a $\sin^2$ wave shape. Heart measurements from the implanted electrode may also be obtained, such as intrinsic or evoked R-wave voltage and impedance of the implanted electrode. Further, various internal pacer characteristics may be provided for pacing the heart, such as pulse frequency, pulse voltage, and pulse width.

In operation, the U.S. Pat. No. 4,141,367 pacer analyzer provides a variety of adjustment knobs for varying the particular parameter represented by the particular knob. Thus, a physician using the analyzer must carefully select the adjustment knob prior to making a measurement. Further, various sensitivity measurements, such as response of the external pacer to simulated R-wave inputs, must be done manually. Further, although it is stated that sequential atrial-ventricle (A-V) sequential pacing can be incorporated, there is no description of apparatus having A-V sequential pacing capability or ancillary capabilities such as measuring a pacer A-V delay or varying the internal pacer A-V delay to monitor the heart response.

It is also desirable to provide automatic reversion of the internal pacer to a nominal set of pacing conditions and in the rate controllable mode whenever the operating mode of the device is changed. In this manner, the pacer analyzer will produce pacer pulses and be ready for adjustments to correct any abnormal heart behavior which may result from the change in pacer stimulation.

The prior art device provides a switch for actually connecting the pacer to the electrodes in the heart for a final compatability check, at the discretion of the physician. It would be desirable to obtain a compatability check without actually connecting the pacer to the patient. Such a compatibility check is extremely desirable since the frequency components of a given R-wave vary from patient to patient, and the resulting R-wave presented to the pacer sensing circuitry after conventional filtering may be greatly altered from the signal produced by a simulated R-wave. These and other problems in the prior art device are overcome by the present invention and an improved pacer analyzer for use in providing a final compatibility check between a pacer to be implanted and the patient having implanted electrodes and usable in an operating room environment is presented.

SUMMARY OF THE INVENTION

Apparatus is provided for determining the compatibility between a cardiac pacer and the stimulation requirements of the patient within which the pacer is to be implanted. In a preferred embodiment, one digitial processor circuit controls the operation of analog circuits to provide a plurality of waveforms. Another digital processor circuit is connected with various memory storage devices and with various input switches to provide parametric control information for the analog circuits. The latter processor circuit is also connected to be responsive to various output signals from the patient cardiac pacer and the electrode leads implanted in the patient to interactively derive threshold operating values.

In a preferred embodiment, an accessible keyboard provides for selecting an operating mode from available modes for testing the patient pacer, measuring actual cardiac operating characteristics on the implanted electrodes, and in a threshold mode for pacing the patient with a variety of pacer pulse parameters. A variety of waveform characteristics can be affected by operation of the function keys, including rate, voltage, interval, current, and pulse width. Further, internal interactive programming can be functionally selected to determine the refractory period of the patient pacer and the sensitivity of the patient pacer to a haversine waveform simulating an R-wave.

Other input keys are selectable for varying operating functions relating to internal pacer operation in a demand or fixed mode, selection of sequential atrial-ventricle stimulation, selection of an atrial and/or a ventricle electrode lead, and a check of internal battery voltage. An anti-arrythmia safety feature is conveniently provided by generating output pulses at a rate six times the selected rate for the purpose of terminating such an arrythmia. Safely interlocks are provided to assure the system is not inadvertently actuated. It is a feature of the present invention to provide apparatus for use in an operating room environment for assuring that a cardiac pacer is compatible with the patient within which the pacer is to be implanted.

It is another feature to provide a variety of waveform parameters which can be continuously varied in preselected increments over wide ranges.

It is still another feature to provide a rotating optical switch for varying the operating parameter values.

One other feature is to provide a full range of compatibility testing on both an atrial lead and a ventricle lead.

Another feature is to provide enhanced current measuring sensitivity at short pulse widths.

A feature of the present invention is to maintain enhanced current measuring sensitivity over the range of selectable stimulating voltages and expected range of implanted electrode lead impedances.

It is a feature to provide a haversine waveform ($sin^2$) with a variable amplitude for testing the patient pacer.

It is a particular feature of the present invention to provide a pacer system analyzer for determining compatibility between a selected implantable pacer and actual stimulation requirements of a given patient to an implanted electrode assembly, including input means for generating a first digital signal selecting an operating mode for said analyzer, selecting a function available within said selected operating mode, and for setting an operating value where said selected function is variable; first digital processor circuitry receiving said first signal and performing an operating routine in response to said first signal to obtain a second digital signal; second digital processor circuitry in electrical communication with said first processor circuitry and generating a third digital signal in response to said second signal; and analog circuitry responsive to said second and said third digital signals and generating a plurality of waveforms suitable for input signals to said implantable pacer or said electrode assembly.

It is a further feature of the present invention to provide for varying the value of a selected function by deriving a sequence of digital numbers in response to arcuate rotation of a dial, comparing said sequence with a stored sequence of digital numbers, determining from said comparison the direction for altering said function, determining from said comparison that a preselected incremental change has occurred, selecting an incremental value associated with said preselected incremental change for said function, and altering said value of said variable function in said determined direction by said selected incremental value.

It is yet another particular feature of the present invention to provide an internal pacer unit for generating stimulating pulses having a pulse generating apparatus, including means for generating a pulse amplitude control signal, an amplifier adapted to produce an output signal on an electrode lead having an amplitude functionally related to said amplitude control signal, first switch means connecting said amplitude control signal to said amplifier at selected intervals for selected durations, second switch means operable in functional proximity with said first switch means for coupling and de-coupling said output signal in feedback to said amplifier, third switch means operable in functional proximity with said first switch for inserting a low resistance capacitance discharge path across said electrode lead at a time between output signals.

Another feature of the present invention is to provide circuitry for deriving an average current value over a wide range of pulse widths and maintaining a high degree of sensitivity over the range, including means for generating an input signal functionally related to the instantaneous value of said selected current, means for generating a digital number functionally related to a selected width for said current pulse, said digital number being constant for pulse widths less than a preselected width and being inversely proportional to said pulse width for pulse widths greater than said preselected width, means responsive to said digital number for amplifying said input signal, an integrator for integrating said amplified input signal to produce an output signal, and means responsive to said output signal and said selected pulse width for producing said average current value.

SUMMARY OF THE DRAWINGS

FIG. 4 is a detailed schematic of stimulating current producing circuitry.

FIG. 4A is a circuit schematic for measuring electrode current.

FIG. 4B is a graph showing the operating characteristics of the circuit depicted in FIG. 4A.

GENERAL DESCRIPTION OF THE ANALYZER SYSTEM

As hereinafter explained, it is highly desirable to check the compatibility of a given patient with a given pacemaker prior to implanting the pacer in the patient. This compatibility is determined after an electrode has been placed in the ventricle and/or the atrium. Thus, a suitable device must be capable of use in the operating room environment and produce results which are useful for compatibility assessment purposes and which do not endanger the patient.

Figure 1:
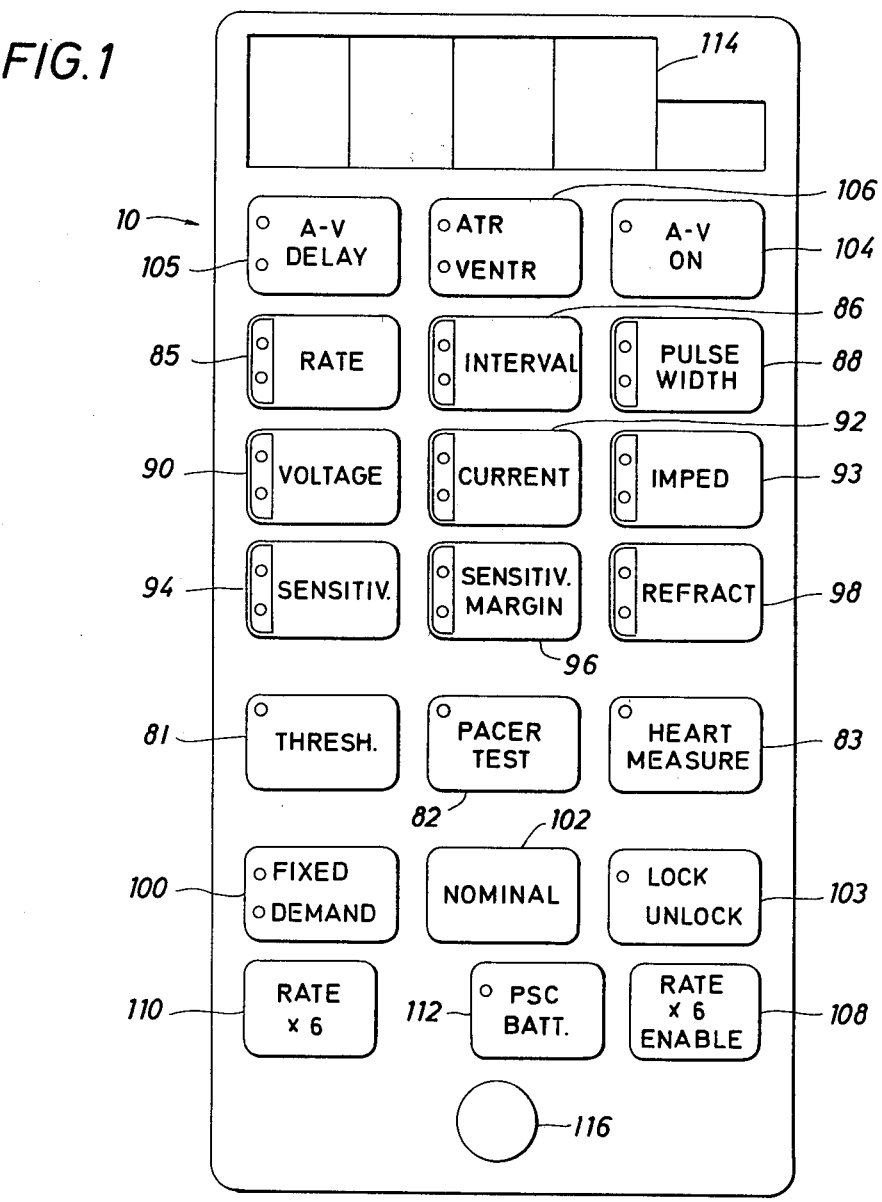
FIG. 1 is a pictorial of the pacer analyzer keyboard and display.

FIG. 1 depicts a keyboard arrangement for use with the present invention to obtain the data needed for a compatibility assessment. In addition to the keyboard, an output display is provided along with an optical switch for changing various ones of the analysis parameters. The keyboard provides for three basic modes of operation: (1) a pacer test mode for monitoring the actual operating parameters of the pacer which is to be implanted; (2) a threshold mode for stimulating the heart through the implanted electrode to determine the heart response to a variety of input pacing parameters; (3) a heart measuring mode, or "R-wave" detecting mode, measuring various characteristics of a naturally occurring heartbeat and for obtaining and storing a representation of the output voltage pulse from the heart for use in the margin test. By selecting a given mode, the function keys which can be actuated in that mode are simultaneously activated and LED backlighted to show the status of the analyzer at any given time.

In addition to the basic mode selection, there are several other features which may be selected. A particular feature is the sequential atrial ventricle (A-V) stimulation feature which is available. The A-V interval can be adjusted over a wide range for stimulating pulses to the patient in the threshold mode, and stimulation and sensing can occur on the atrial and/or the ventricle lead. A further feature is a frequency multiplier (Rate X6) for use in terminating an arrythmia, should one occur. Yet another feature is the ability to return all of the output parameters of the analyzer internal pacer unit to nominal conditions by a single button.

The keyboard 10 interacts with an alpha-numeric display 114 and an optical switch 116 to provide the operator with a variety of information and control functions. Keyboard 10 consists of three types of keys which will determine the type of information displayed by alpha-numeric display 114. Mode Select, Multiple Function Programmable, and Single Function (Command) keys. The Mode Select keys (Threshold 81, Pacer Test 82, and Heart Measure 83) are used to define the operation of each of the Multiple Function keys (Rate 85, Voltage 90, Sensitivity 94, Interval 86, Current 92, Sensitivity Margin 96, Pulse Width 88, Impedance 93, and Refractory 98). The Single Function keys (Demand-Fixed 100, A-V ON 104, Battery 112, and Atrium/Ventricle 106), each relate to a particular function. Table A correlates the various key functions.

TABLE A

| MODE SELECT | MULTIPLE MODE | FUNCTION |
| --- | --- | --- |
| Threshold 81 | | Adjust and display analyzer pacer functions; Rate, Interval Pulsewidth, Voltage, Current, Impedance, A-V delay (if actuated). |
| | Rate 85 | Pacer Pulse Rate displayed and adjusted using switch 116, in 1 ppm steps from 20 ppm to 200 ppm. |
| | Rate X6 Enable 108 | Operates in Rate Mode to enable Rate X6 function; a short tone is generated during the 2 seconds that the Rate X6 key is enabled. |
| | Rate X6 110 | Increase Rate by a factor of 6 after the Rate X6 Enable key has been depressed. |
| | Interval 86 | Pacer Pulse Interval displayed in milliseconds and adjusted using switch 116 in 1 ms steps from 300 ms to 3000 ms. |
| | Pulse width 88 | Pacer Pulse Width displayed in milliseconds and adjusted using switch 116 in .05 ms steps from .05 ms to 3 ms. |
| | Voltage 90 | Internal Pacer Output Voltage displayed in volts and adjusted using switch 116 in .1 V steps from .1 V to 10 V. |
| | Current 92 | Internal Pacer Output Current displayed. |
| | Impedance 93 | Impedance of implanted patient leads displayed. |
| | A-V Delay 105 | In A-V pacer mode, delay between the Atrial pulse and Ventricular pulse displayed in milliseconds and adjusted using switch 116 in 1 ms steps from 75 ms to 300 ms. |
| | Nominal 102 | Resets value of selected function to a nominal value. |
| Pacer Test 82 | | Measure Rate, Interval, Pulse Width, Voltage, Current, Sensitivity, Refractory, A-V Delay of selected implantable pacer. |
| | Rate 85 | Patient Pacer Rate displayed (ppm) with resolution to 1 decimal place. |
| | Interval 86 | Patient Pacer Pulse Interval displayed (ms). |
| | Pulse Width 88 | Patient Pacer Pulse Width displayed (ms) with resolution to two decimal place. |
| | Voltage 90 | Patient Pacer Output Voltage displayed (v) with resolution to 1 decimal place. |
| | Sensitivity 94 | Test and display sensitivity of Patient Pacer to simulated R-Wave (Haversine). |
| | Refractory 98 | Measure and display refractory period of patient pacemaker (ms). |
| | A-V Delay 105 | Display delay between atrial pulse and ventricular pulse (ms). |
| Heart Measurement 83 | | Measure and display Heart Rate, Interval, Voltage, Margin; disables analyzer pacer during measurement. |
| | Rate 85 | Heart Rate displayed. |
| | Interval 86 | Interval between peaks of R-Wave displayed. |
| | Voltage 90 | Band pass filter to approximate waveform available to actual pacer. |
| | Margin 96 | Patient Pacer tested for sensitivity point; stored QRST from patient presented to patient pacer to determine patient pacer sensitivity. |

| SINGLE FUNCTION | FUNCTION |
| --- | --- |
| Fixed/Demand 100 | Select either fixed or demand internal pacer mode. |
| A-V ON 104 | Select A-V internal pacer mode. |
| Battery 112 | Display internal battery voltage. |
| Atr/Ventr 106 | Select either Atrium lead or Ventricle lead for testing. |

As hereinafter explained, some of the functions are passive measurements where the incoming data is converted from an analog form to a digital display. Certain of the measurements are interactive measurements, requiring that the system determine the response of the patient pacer to various outputs, alter the outputs, and continue in a given sequence until a predetermined response is obtained. Still other of the functions are programmable, i.e., adjustable, so that the heart or pacer response can be monitored under a variety of stimulation parameters. The programmable functions are adjusted by using switch 116, which may conveniently be an optical switch to eliminate the need for electrical contacts. Alpha-numeric display 114 provides a direct visual indication of the inputs being sensed, the output parameter being varied, and/or the results from the active measurement.

MAIN PROGRAM

Figure 2:
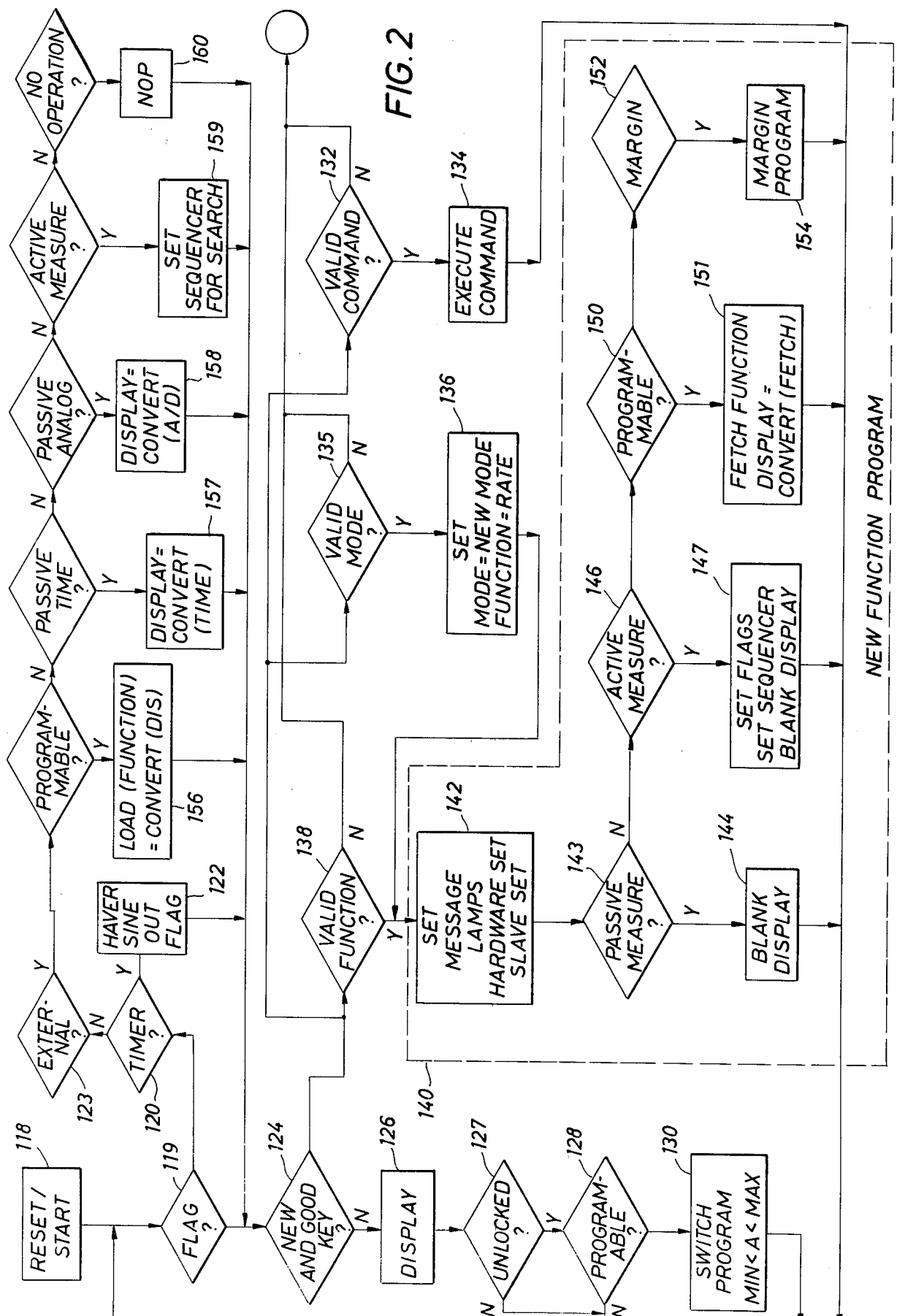
FIG. 2 is a flow diagram of the analyzer operating routine.

Referring now to FIG. 2, there is seen a flow chart for the MAIN PROGRAM operating the analyzer. Once the analyzer is initialized, or started, the programmable functions are set 118 to nominal values, the various system interrupts are all enabled, and the various timing circuits are started. The MAIN PROGRAM first determines whether a flag 119 exists to interrupt the MAIN PROGRAM. A first interrupt 120 occurs from timer circuitry during pacer sensitivity measurements to produce a standard haversine signal 122 to the pacer. The more usual interrupt is an external interrupt 123 from the slave processor or pacer under test. In the internal pacing mode, the interrupt 123 occurs just before the pacer generates a new pulse, where the slave processor is requesting an update 156 from the master processor or output pulse parameters, to set the counting circuits 156 prior to a measuring interval, to select the proper analog-to-digital output 158 for display, or to activate the proper sequence routing 159 for an active measurement. If the operation does not require an analyzer output pulse, then the system is returned to the MAIN PROGRAM through the NOP 160 routine.

However, on the first cycle from start-up, the MAIN PROGRAM goes directly to examine the keyboard input 124 to determine the existence of a new and good key. This is really two separate determinations requiring that a new key is selected and that good contact is made. Thus, this determination is always negative the first cycle and MAIN PROGRAM moves to activate the display 126. Following the display activation 126, the MAIN PROGRAM determines whether the analyzer is unlocked 127, i.e., whether the analyzer outputs can be varied and whether a programmable function 128 has been selected. If so, the switch program 130 is activated and the switch input accepted.

The MAIN PROGRAM then returns and on the second cycle begins to look for flags 119. The occurrence of a flag 119 momentarily interrupts the MAIN PROGRAM while the interrupt source routine executes a sub-routine unique to each function. On the second keyboard scan 124, the occurrence of an identical reading from the first scan now produces an affirmative response and the MAIN PROGRAM now acts to set the system to respond to the new keyboard arrangement. It should be noted that the determination of a new and good key 124 indicates a good key where only a single key remains depressed continuously for two scans and a new key where the key input has not been processed by the PROCESS PROGRAM (see FIG. 8).

The PROCESS PROGRAM (see FIG. 8) receives the output from the keyboard to determine the types of processes which are to be carried out. If a command process 132 is activated, then the COMMAND PROGRAM 134 (FIG. 9), hereinafter discussed, is selected and executed. According to the preferred embodiment of the present invention, one of the following commands may be selected: (1) arm the "X6" program for terminating an arrythmia; (2) activate the "X6" program if the arming key remains active; (3) determine the analyzer battery voltage; (4) place the analyzer in either a sensing (demand) or not-sensing (fixed) condition; (5) turn the A-V mode on or off; (6) select either the A or V lead for signal input; (7) lock or unlock the switch input; (8) reset the selected internal pacer function to nominal conditions.

If the PROCESS PROGRAM determines that a new mode 135 is selected (FIG. 2), the system program pointers are reset 136 for the new mode, the RATE function being automatically selected until a new function key is depressed. Once a function is selected 138 for the desired mode, the NEW FUNCTION program 140 is activated. The selected function is accessed via an instruction table in a preselected memory location 142, as hereinafter described, to set the display characteristics and keyboard lights, to select the source of the interrupt flag as either the slave processor or an external event, and to select either an atrium or ventricle lead. Finally, the appropriate slave processor code is selected to obtain the desired operating routine.

The slave processor, in turn, then selects the appropriate multiplexer outputs from the analog system and other constants for performing the selected routines. If a passive measurement is selected 143, e.g., pulse interval or voltage, the display is momentarily blanked 144 until the main program returns to display after a value has been determined. If an active measurement 146 is to be performed, e.g., external pacer sensitivity or refractory time, the appropriate flags 147 are selected for the interrupt routine, the sequence programs are activated, and the display is blanked until an output is available to display. If a programmable function 150 has been selected, the value of the function is updated from the slave processor and the switch routine, and the value thus fetched is displayed 151.

Finally, the margin function 152 may be selected. As hereinafter discussed, the margin function acts as a final compatibility check by digitizing and storing the patient's actual R-wave and reproducing the wave form at various amplitudes to determine the response of the patient pacer to the actual wave form of the patient. The reproduced R-wave amplitude is progressively altered until the pacer response indicates a program convergence according to the MARGIN program 154, hereinafter discussed (see FIG. 14).

SYSTEM DIAGRAM

Figure 3:
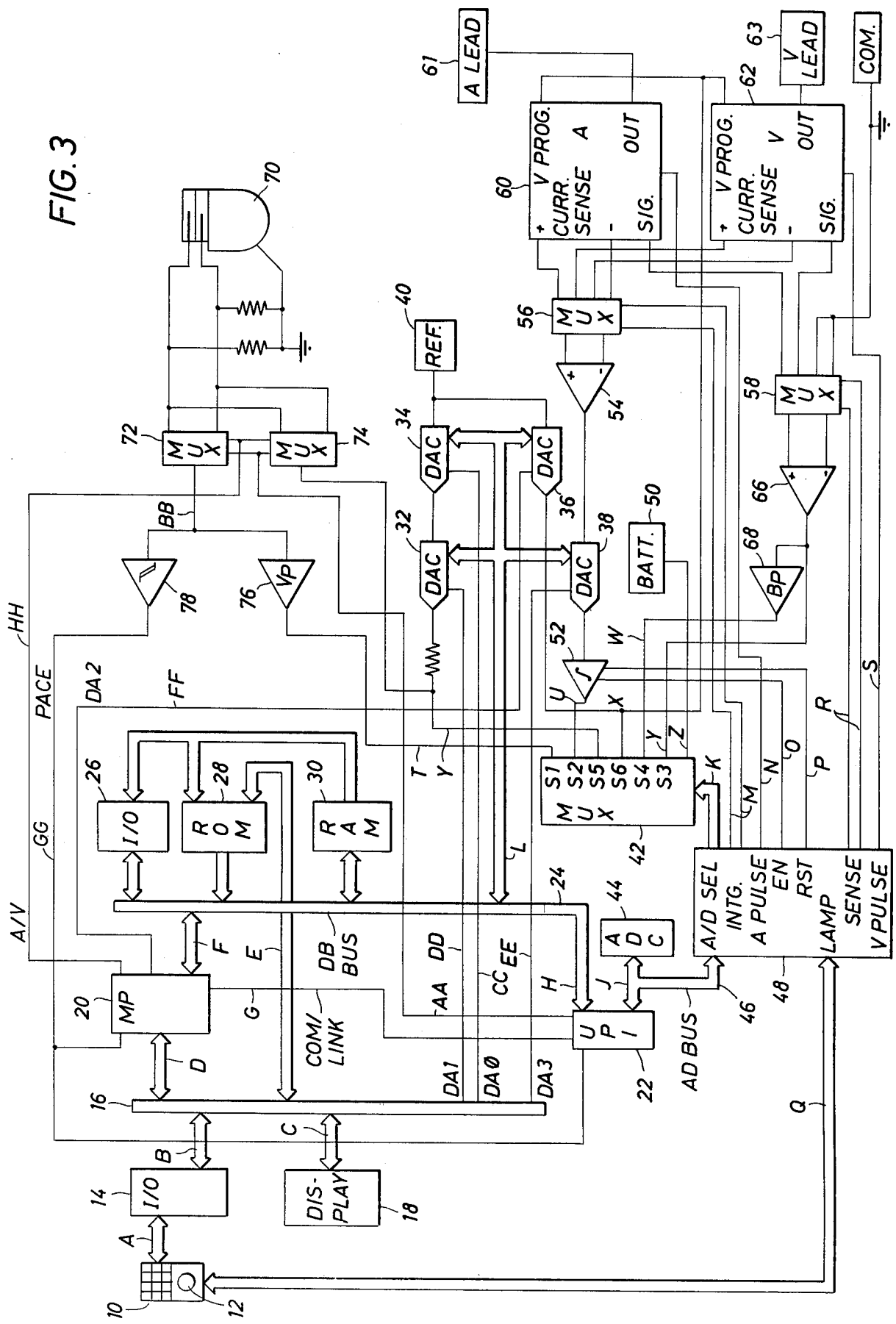
FIG. 3 is a circuit diagram in block form of the pacer analyzer which is the subject of the present invention.

Referring now to FIG. 3, there may be seen in block diagram form a schematic of the preferred embodiment of the pacer analyzer system. As hereinabove described, the pacer analyzer system incorporates a keyboard 10 for directing the operation of the analyzer system. External connections are available for a cardiac pacer 70 and for cardiac electrode leads 61 and 63 which may be interconnected to a patient. The overall system incorporates an analog system for either deriving or processing analog signals to and from the pacer 70 and cardiac leads 61 and 63.

The analog system is controlled generally by keyboard inputs which select various ones of the analog systems, and by commands from a master processor, a microprocessor actually controlling the sequence of events. A slave processor accepts data from the analog system in response to commands from the master processor and enables other portions of the analog system to accept data input in response to commands from the master processor.

It should be noted that the terms processor, microprocessor, and microcomputer may be used interchangeably. Any integrated circuit having an adequate programming and data handling capability may be utilized in the system within the scope of the present invention and such integrated circuits are hereinafter generically referred to as microprocessors.

The pacer analyzer system is formed to provide several distinct modes of operation, as hereinabove described. Basically, the system can provide test signals to a pacer 70 and detect the response of pacer 70 to the test signals. Various output characteristics of pacer 70 can be determined, such as the pulse width, pulse height, pacer rate, refractory period, and the delay between an atrial and ventricle pulse where sequential atrial/ventricle (A-V) operation is desired.

Similarly, the system can be connected with implanted cardiac electrode leads 61 and 63, one of which may be an atrial lead and the other may be a ventricle lead where A-V operation is desired. The pacer analyzer will operate in a pacing mode to provide stimulating pulses to the patient's heart and to monitor the response of the heart to the input. The characteristics of the implanted electrode can be determined by various measurements relating to average input pulse current; and heart response to stimulating pulses from the anaylzer can be analyzed.

Finally, the patient's cardiac output can be converted to a digital signal and stored in the analyzer. The stored characteristics are then presented to the patient pacer to monitor the response of the actual pacer, which is to be implanted, to the characteristics of the patient, who is about to receive the pacer, without having to actually connect the pacer to the patient. By actively varying the amplitude of the patient's stored characteristics, a determination can be made for pacer sensitivity to the actual heartbeat characteristics to obtain a value representing a safety margin. The safety margin represents a ratio between the amplitude of a normal heartbeat and the amplitude of a re-created heartbeat, below which the pacer does not respond. This final compatibility check is added assurance that the particular pacer and the particular patient are compatible.

Referring again to FIG. 3, the desired operating characteristics for the pacer analyzer are selected by depressing various keys in keyboard 10 and, if a programmable function is selected, by turning optical switch 12 (116 in FIG. 1) until the desired parameter value appears on display 18. Signal A represents the output from the keyboard and optical switch connections and is presented to input/output (I/O) expander port 14. Signal A is thus converted by I/O port 14 to signal B along data bus 16.

The master processor 20 is constantly in contact with data bus 16 through signal D. Data bus 16 can be interrogated to obtain keyboard inputs and can be supplied with information forming signal C to activate display 18. Data bus 16 also provides data bank information from the read-only-memory (ROM) through signals E.

Master processor 20 also communicates with the various memories and the slave processor 22 through data bus 24. Master processor 20 output signals F are presented along data bus 24 to directly access ROM bank 28 and the random-access-memory (RAM) bank 30. I/O port 26 also accepts signals from master processor 20 and provides memory access instructions to RAM bank 30 and ROM bank 28.

Communication signal G between master processor 20 and slave processor 22 provides for transmitting various interrupt flags in response to the operating routines hereinafter described. Data bus 24 is the main information transfer bus between slave processor 22 and master processor 20, moving master-slave transfer signals H therebetween. If the analyzer is generating outputs to the external connections, the slave processor 22 can be updated by master processor 20 along data bus 24 prior to slave processor 22 initiating any output signal.

Thus, master processor 20 and slave processor 22 communicate with one another to affect the operation of various analog systems, as hereinafter described. One analog system is formed by digital-to-analog (DAC) converters 32 and 34. A desired test signal is a haversine wave form, a standard approximation of the wave form obtained from actual heartbeats. Thus, digital instructions L are provided to DAC 32 and 34. DAC 34 is connected to a fixed reference signal 40 and is arranged in a conventional multiplying arrangement where the analog output is a multiple of the digital input L. The output of DAC 34 is then presented to DAC 32 to provide a variable reference for affecting the amplitude of haversine signal Y. Analog signal generation control L then provides digital inputs to DAC 32 in a sequence generating a haversine shape output signal Y.

DAC 36 is provided to control the pacing pulse amplitude. Accordingly, DAC 36 receives digital inputs L which also determine the amplitude of the analog output signal X. Signal X, in turn, is applied to atrial and ventricle signal/pulse circuits 60 and 62, respectively. Amplitude control signal X provides for producing pacing pulses having a variety of amplitudes for determining heart response characteristics, such as a threshold voltage for causing a heartbeat from a stimulating pulse.

The operation of DAC 32 and 34 is controlled by control signals DD and CC, respectively, from data bus 16. Thus, direct control of haversine test signal Y is provided by master processor 20. The operation of the pulse amplitude control DAC 36 is enabled by signal FF generated by master processor 20. Control signals CC, DD, and FF, enable DAC 34, 32, and 36, respectively, to accept or lock out signals from analog system control signal L.

The haversine test signal Y may be used as an input to pacer 70. In this instance, the test signal is presented to multiplexer 74. The output of pacer 70 is connected to multiplexer 72. Two connections are provided for multiplexers 72 and 74 to accommodate A-V-type sequential pacers. The desired pacer connection is controlled by signal HH, which is the A-V selection signal from master processor 20. The desired multiplexer connection is selected so that the test signal is applied to either the A or the V lead and the corresponding lead is selected to monitor the pacer response.

Thus, pacer 70 may be provided with a haversine test signal having amplitude and timing determined by master processor 20. The pacer 70 output lead selected by mulitplexer 72 forms pacer output signal BB in response to the haversine test signal. Pacer output signal BB is presented to a trigger circuit 78, which may conventionally be a comparator with a hysteresis response such as a Schmitt trigger, to form an on-off signal GG, indicating the event of a pacer output signal. Pace signal GG is applied to master processor 20 and slave processor 22, to signal the occurrence of the event. Master processor 20 may have associated circuitry (not shown) which monitors the duration and frequency of the pacer output pulses. Various system operations are disenabled during the occurrence of the pulse indicated by pace signal GG.

Pacer output signal BB is also presented to a conventional peak detector circuit 76. Peak detector circuit 76 follows the incoming pacer output to form peak detector signal T which is the peak amplitude of the output signal BB from pacer 70.

In addition to determining the operating characteristics of the pacer 70, the pacer analyzer may also determine the operation characteristics of the implanted electrode leads 61 and 63. This, of course, is necessary to verify that pacer 70 has an output sufficient to obtain a stimulating pulse which will produce a cardiac response. Thus, another analog system is provided to determine the average current drawn by the electrode leads 61 and 63 while the heart is being paced.

Current signals are produced by atrial and ventricle signal/pulse circuits 60 and 62, respectively, and presented to multiplexer 56. Multiplexer 56 is controlled by the integrating circuit current selection signal M. The production of current selection signal M, in turn, is controlled by slave processor 22 along data bus 46 through digital data transfer signals J.

The output from multiplexer 56 is amplified by operational amplifier (op-amp) 54, which may conveniently be conventional circuitry forming a difference-type amplifier. The output from op-amp 54 is provided as a variable reference voltage to DAC 38. DAC 38 is conventionally connected in a divider-type arrangement. Thus, the output from DAC 38 is some quotient of the input reference signal as determined by digital control signal L. Control signal L will be determined by the particular current measuring scheme being used (FIGS. 4A, 4B, 12, 13). DAC 38 is enabled by signal EE along data bus 16 when the analyzer user determines that average current is to be derived. System routines for generating an average ouput current are hereinbelow described.

In one embodiment, the output from DAC 38 is applied to integrating circuit 52 to form signal U which is functionally related to the average integrated pulse current. Integrator circuit 52 is enabled by signal O and reset by signal P. Signals O and P are outputs from I/O expander port 48 which is controlled by slave processor 22, as hereinabove described. As noted in the discussion below on the process routine for obtaining an integrated pulse current, the system is enabled just prior to receiving a pulse and reset just after the pulse is converted to digital form to minimize system drift.

Yet another analog system is provided to sense the electrode signals produced by naturally occurring heartbeats. The atrial and ventricle signal/pulse circuits 60 and 62, respectively, accept data from the cardiac leads 61 and 63. This data is available to multiplexer 58. Multiplexer 58 is controlled by sensing lead selection signal R, one of the outputs from I/O expander port 48. If a sensing operation is selected, sensing lead select signal R transmits either the A lead 61 or the V lead 63 signal through multiplexer 58 to amplifier 66. Amplifier 66 may conveniently be a plurality of components in a conventional instrumentation amplifier configuration. The output from amplifier 66 is the unfiltered sensed cardiac signal V. This system may be used directly or may be provided to a bandpass amplifier 68 which filters out a portion of the signal to provide a filtered sensed cardiac signal W. Bandpass filter 68 typically represents filter circuits in conventional pacers and filtered signal W, thus, represents the input signal waveform available to conventional pacer detection circuitry.

I/O expander port 48 also provides an atrial pulse signal N and a ventricle pulse signal S. Signals N and S switch pulse producing components in the atrial and ventricle signal/pulse circuits 60 and 62, respectively, to produce the desired output pulses. Thus, cardiac pacing outputs are provided on the A lead 61 and/or the V lead 63 to stimulate the heart in accordance with the keyboard selected parameters or nominal pacing parameters, as hereinafter discussed.

Finally, the system is battery powered to facilitate use in an operating room environment. Thus, provision is included for checking the battery 50 output. A battery voltage signal Z is provided for that purpose.

Thus, a multiplexer 42 receives various analog signals:

Signal T—pacer peak voltage detector output;
Signal U—pulse current integrator output;
Signal V—unfiltered sensed signal;
Signal W—band pass filtered sensed signal;
Signal X—generated pulse amplitude;
Signal Y—haversine test signal;
Signal Z—battery voltage.

Multiplexer 42 selects one of these signals to present to analog-to-digital converter (ADC) 44. The output from multiplexer 42 is controlled by the analog selection demand signal K from I/O expander port 48 as commanded by slave processor 22. The converted digital signal J from ADC 44 is presented on data bus 46 to slave processor 22. Thus, the various analog inputs are available in digital form for processing by the slave processor 22 or master processor 20 in the course of the system performing the various routines hereinafter discussed.

The output from I/O expander port 48 also includes lamp command data Q. Lamp command data Q lights various ones of the lamps on the keyboard, signaling and verifying selection of the operative buttons. This permits the operator to visually verify that the entered commands are being carried out. An audible tone is also emitted to indicate command changes.

Referring now to FIG. 4, there is more particularly shown a schematic diagram of an electrical circuit forming the atrial (or ventricle) pulse/signal circuit 60 (or 62), shown in block form in FIG. 3. Operation of the system is controlled by pulse amplitude signal X and a pulse initiation control signal M1, coming from slave processor 22 (FIG. 3). The system outputs include a voltage signal across resistor R3, which is functionally related to the pulse current, and the pulse current, which is supplied to the heart via the lead output.

The circuit is normally set with switch S1, which is preferably a solid state device, in a closed condition, thereby applying a fixed reference voltage to the inverting terminal of operational amplifier A2. In this condition, transistor Q1 is switched to the off state and the system is in a steady-state condition with no current flowing through resistor R3. When a pulse output is desired, signal M1 from the processor system is applied to op-amp A1 to open switch S1. When switch S1 opens, amplitude control signal X is then applied to the inverting terminal of op-amp A2 to produce an output which switches on transistor Q1.

Transistor Q1 is inserted in the system for current amplification, producing an output current pulse with a sharp leading edge and without significant ringing. The current flowing through resistor R3 produces a voltage across resistor R3 which is directly proportional to the current and the voltage signal forms the pulse signal for processing, as hereinabove discussed. Thus, a negative voltage pulse appears across the pacer output leads.

The duration of the output pulse, or pulse width, is controlled by pulse signal M1. Thus, signal M1 opens switch S1 at the beginning of a pulse and closes switch S1 at a time appropriate to terminate the pulse. Closing switch S1 returns an input voltage to op-amp A2 which turns off transistor Q1 to return the system to a non-pulse condition.

Signal M1 also opens switch S2, opening capacitor C2 discharge path to ground. Thus, the output lead is connected through C2 to the non-inverting terminal of op-amp A2 and the lead signal is driven toward the op-amp A2 input voltage X by current through transistor switch Q1.

The lead output is connected to an implanted electrode assembly which has a substantial capacitance in conjunction with adjacent tissue. This capacitance can greatly increase the decay time for capacitor C1 so that full discharge may not occur before the next output pulse. This effect is minimized in the present circuit through the use of switch S3 and capacitor C2.

First, switch S3 permits capacitor C1 to discharge through resistor R3, which generally has a low resistance and decreases the voltage decay time. Switch S3 is open during the output pulse and is closed by signal M2. Signal M2 generally occurs substantially contemporaneous with the termination of signal M1. Thus, the output voltage has more nearly returned to ground before a subsequent pulse arrives.

Next, capacitor C2 de-couples op-amp A2 from any remaining voltage on the output lead. Switch S2 operates with switch S1 and is closed between pulses to place the non-inverting terminal of op-amp A2 at a ground potential. Removing any residual voltage from the non-inverting terminal of op-amp A2 causes a full voltage swing to be developed on the output lead in accordance with the amplitude of pulse amplitude control signal X.

The system electrode leads to the heart may also operate in a sensing condition. Accordingly, a sensing output connection is provided from the circuit which is provided to the appropriate multiplexer 58 (FIG. 3). Thus, the actual output from the heart is provided to the analyzer system. It should be noted that all the ground connections in the circuit hereinabove depicted are common to the patient ground connection to obtain the proper reference conditions.

In one embodiment, the current delivered to the Lead Output depicted in FIG. 4 is measured by prescaling the current signal before conversion and display. Suitable prescaling circuitry and associated operating characteristics are shown in FIGS. 4A and 4B, respectively. The gain characteristics shown in FIG. 4B accommodate a wide variety of impedance in the implanted electrode leads through the range of programmed voltage outputs applied to the leads.

Generally, the impedance of the implanted electrodes will be in the range of 300 to 3000 ohms. The applied voltage, however, can vary from 0.1 to 10.0 volts during threshold testing. The resulting current could range from 0.033 to 33.33 milliamperes (ma). An uncompensated system cannot provide adequate resolution over the entire three decade range of current values.

To compensate for the range of currents, the system gain may be varied to maintain a constant full scale output over a selected range of stimulating voltages. In one embodiment depicted in FIG. 4A, a full scale reading of −10 volts is provided at the assumed implanted lead impedance of 300 ohms which yields maximum current and maximum input voltage to the measuring circuit.

Accordingly, the master processor unit varies the gain as a function of the stimulating voltage. In a preferred embodiment, the gain is determined by the formula:

$$N = 20\, V_o.$$

However, as shown in FIG. 4B, an overall system gain of 60.0 is required at a stimulating voltage of 1.0 V. The gain is not adjusted below 1.0 V since large gains lead to increased system errors.

The circuit shown in FIG. 4A uses a sampling resistor R to obtain an input voltage Vin from the current delivered to the implanted electrode leads ($V_{in} = R\, V_o/R_L$). A fixed gain differential amplifier amplifies the signal at a first gain, $G_1 = 4.6875$. A multiplying DAC is connected as a divider to obtain a second gain, $G_2 = -256/N$ where N is a digital number provided by the master processor.

The following Table shows the system operation at selected stimulating voltages:

| | PRESCALAR PARAMETERS | | |
|---|---|---|---|
| Output Voltage ($V_0$) | Current (ma) 300 ohms | Gain G = $G_1 \times G_2$ | Full Scale Deflection ($V_1$) |
| 10.0 | 33.33 | −6.0 | 10.0 |
| 5.0 | 16.67 | −12.0 | 10.0 |
| 1.0 | 3.33 | −60.0 | 10.0 |
| .9 | 3.00 | −60.0 | 9.0 |
| .7 | 2.33 | −60.0 | 7.0 |
| .5 | 1.67 | −60.0 | 5.0 |
| .3 | 1.00 | −60.0 | 3.0 |
| .1 | 0.33 | −60.0 | 1.0 |

PROCESSOR OPERATIONS

Figure 5:
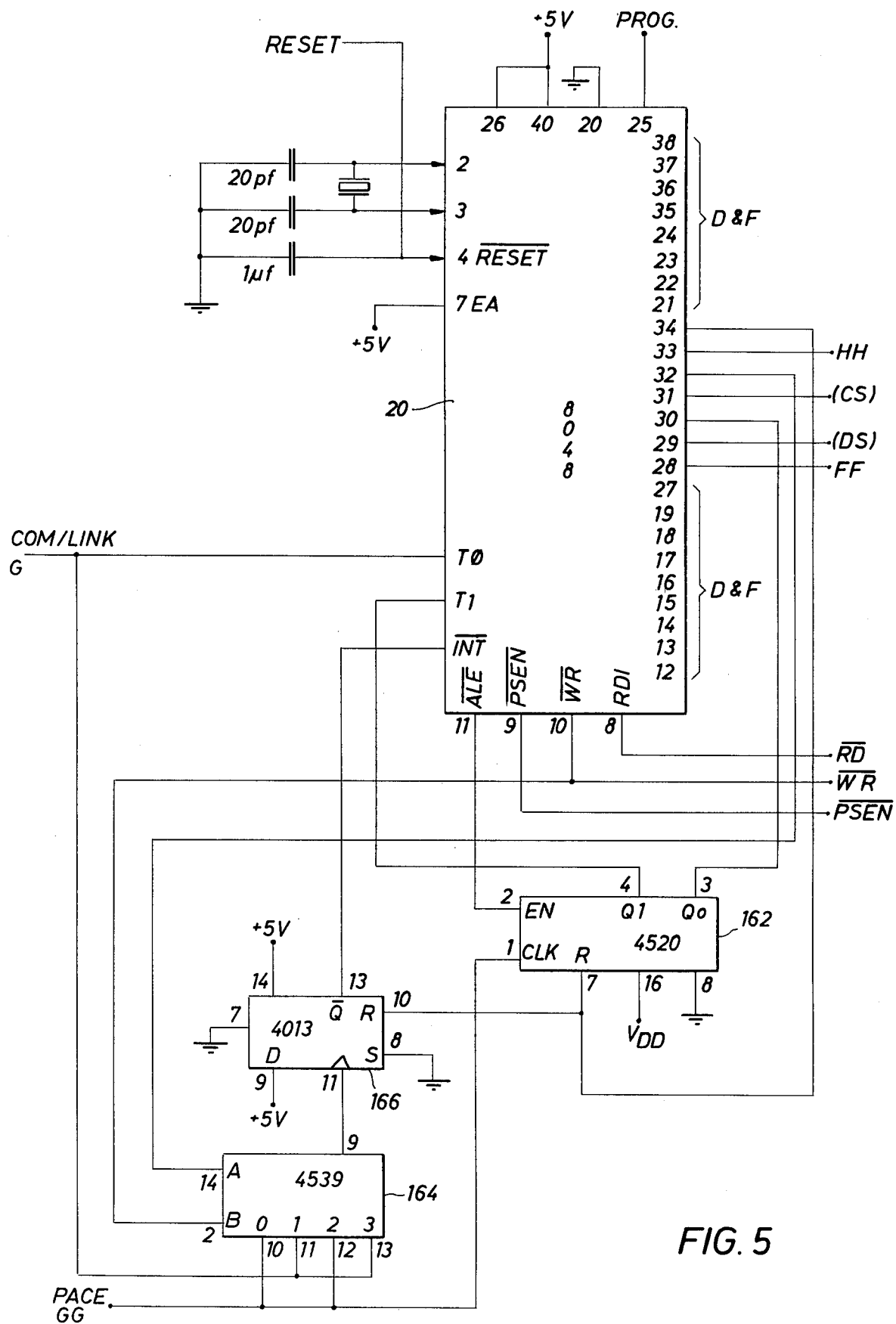
FIG. 5 is a schematic of the microprocessor electrical interconnections.

As hereinabove noted, circuitry as shown in FIG. 5 is interconnected with the master processor 20 for deriving various system flags for routine interrupts and for deriving pulse width data. Counter 162 provides pulse width data. The CLK input from the pulse signal GG is transferred to Q1 during each EN pulse from processor 20. This series of pulses is provided at T1 of processor 20 to be counted for a pulse width measure.

Counter 164 serves as a digital selector to select interrupts from either the COM/LINK signal G or PACE signal GG. COM/LINK signal G and PACE signal GG are provided selector 164. Selector 164, in turn, clocks D flip-flop 166 to produce an output signal to processor 20 input INT to interrupt the inputs to processor 20.

As hereinabove set forth, the pacer analyzer is an active device as well as a passive device. A slave microprocessor is provided for generating timing signals which control various ones of the analog pulse generating and pulse sensing units. The slave processor (UPI) is linked to the master processor and communicates with the master processor to receive operating instructions. The operational timing of the UPI is set out in FIG. 6.

Figure 6:
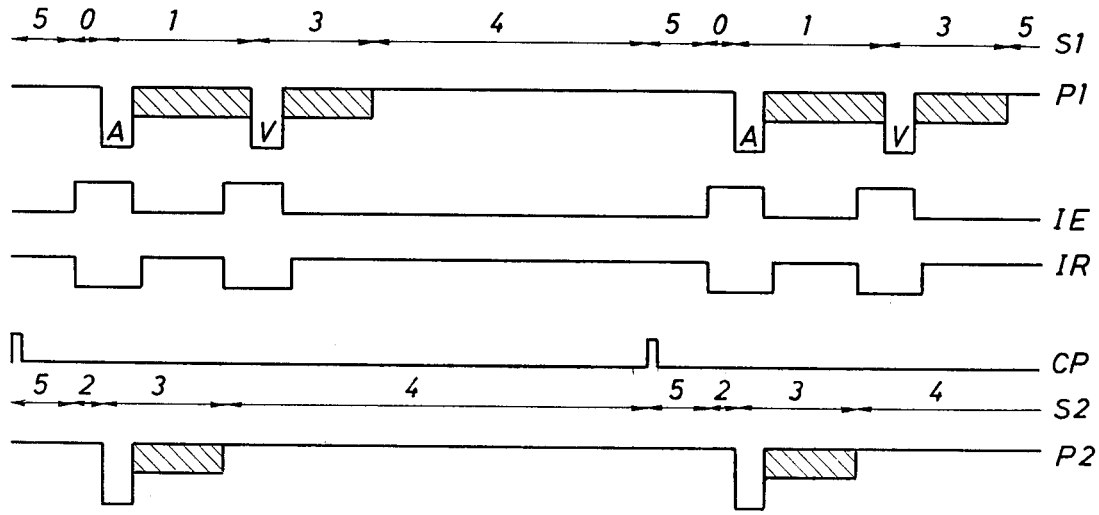
FIG. 6 is an operating state diagram for a slave processor.

As shown in FIG. 6, operation of the UPI is divided into several operating states, as depicted in state lines S-1 and S-2. The various operating states are as follows:

Operating State 0—Integrate enable interval to initialize the integrator prior to a pulse.

Operating State 1—A-V delay for sequential A-V stimulation.

Operating State 2—Integrate enable interval to initialize the integrator prior to a pulse.

Operating State 3—Refractory interval subsequent to ventricular stimulation.

Operating State 4—Sensing interval for detecting an incoming cardiac response.

Operating State 5—Pre-pulse for informing the master processor that a programmable function is about to be generated and updating the parameters for that function.

Operating State 6—Sensed sensing interval where a "R" wave or other signal greater than 1 mv is received and the unit returned to an initial state 4 condition.

FIG. 6 depicts the timing relationships between the various operating states. State Line S-1 is carried out when A-V mode operations are being carried out. State Line S-2 refers to operation in a ventricular stimulation mode only. The various timing signals, integrator enable (IE) (signal O in FIG. 3), integrator reset (IR) (signal P in FIG. 3), and pre-pulse (CP), operate for either State Line S-1 or S-2. Thus, at Operating State 5, pre-pulse CP occurs for UPI to inform the master processor that a pulse is about to be generated. Depending on the selected operating mode, function, and state of the program being executed, the parameters relating to pulse width, pulse voltage, A-V delay, and frequency are returned to the UPI.

At operating state 0 or 2 for State Lines S-1 and S-2, respectively, the integrator circuit, hereinafter discussed, is enabled as shown by timing pulses IE and IR. Timing pulse IE enables the integrator circuit at the same time that timing line IR removes the reset signal from the integrator. This enablement occurs a short time, i.e., about 5 μsec, before a pulse is generated. It should be noted that enablement signal IE terminates when the pulse terminates. The reset signal IR is not returned for a short time later to provide an interval for the converting the integrator reading from an analog signal to a digital number. The reset pulse IR is then returned and the integrator is ready for another pulse input.

In the AV mode, operating state 1 is the time interval for timing the atrium pulse and blanking the sensing input as shown by the shaded interval. At the end of the selected AV delay, operating state 3 is obtained where a ventricular pulse is produced and the resulting refractory interval measured. There is also no sensing during the refractory period.

Following the refractory interval 3, operating state 4 is obtained for sensing cardiac response to the pacing output. If a response is sensed during operating state 4, operating state 6, not shown, is obtained for demand-type pacing and operating state 4 is reestablished. Thus, UPI controls the pacing output from the analyzer.

OPERATING ROUTINES

The MAIN program, hereinabove discussed with reference to FIG. 2, refers to various other routines which are initiated in response to system interrupt flags and new keyboard commands. Significant routines are hereinafter discussed with reference to operational flow diagrams. It will be appreciated that these flow diagrams can be implemented by a variety of specific process instructions prepared by persons skilled in the programming art and the present invention resides in the processes and not in the implementing programs.

MAIN PROGRAM

Figure 7:
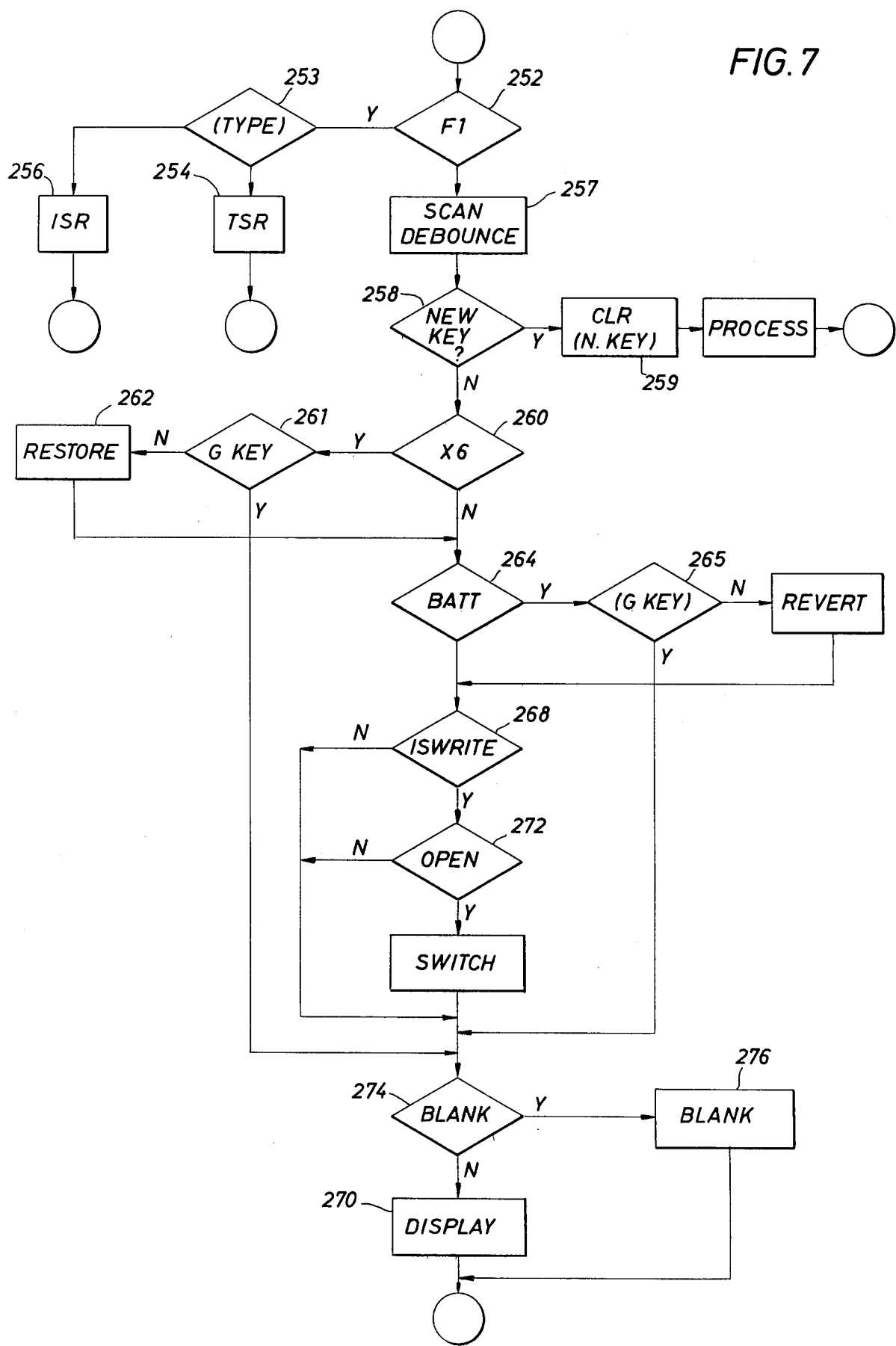
FIG. 7 is a flow chart for the MAIN program.

Referring now to FIG. 7, there is more particularly shown a flow diagram of the MAIN PROGRAM. The MAIN PROGRAM is a closed-loop program which continuously monitors the keyboard and sets the system to respond to the keyboard request. Thus, once the system is initialized, the MAIN PROGRAM first determines the existence of an interrupt flag 252. If present, the type 253 of interrupt flag is determined. A timer interrupt flag (TSR) 254 will be present during a sensitivity determination and the MAIN PROGRAM will be interrupted while a test signal, a haversine output, is provided to external pacer. If the flag is from an external source, either produced from the slave processor or produced from an incoming signal, the ISR routine 256 is initiated while information is being moved to and from the slave processor and to and from the display.

When the interrupt flag has cleared, the keyboard is scanned 257 to determine the existence of a new key which is suitable for changing the system parameters. If a new key 258 is detected, the system is set 259 to accept the new key and the remainder of the PROCESS ROUTINE (see FIG. 8) is carried out to execute the request generated by the depressed key. Next, the existence of special requests are determined, particularly the "X6" request 260 to initiate a pulse train at a rate capable of terminating a tachycardia or other arrhythmia. The "X6" key is verified to be sure it is a good key 261, i.e., still depressed. If the key remains depressed, the remainder of the MAIN PROGRAM is not performed and the display is activated to show the existence of the high output frequency. Once the "X6" key has been released, the MAIN PROGRAM is restored 262.

The program also determines if a request has been entered to display the analyzer battery voltage 264. If so, the program verifies 265 so that the key remains depressed. The remainder of the MAIN PROGRAM is not performed and the battery voltage is displayed. If the key has been released, the routine reverts 266 to the previous state of the MAIN PROGRAM.

The next determination of the MAIN PROGRAM is whether a programmable function 268 has been selected, i.e., whether parameter changes can be entered into the system. If the selected function is not a programmable function, the MAIN PROGRAM moves to the display routine 270. If a programmable function is selected, the MAIN PROGRAM must then determine whether the system is open 272, i.e., whether the function can be changed. If the system cannot be changed, then the program moves to the display portion 270. If the selected function is a programmable function and the system is in an unlocked, or open, condition, then changes in the parameter may be obtained from a suitable input device. The SWITCH PROGRAM (see FIG. 10) accepts inputs from the input device to alter the function parameter value, as hereinafter discussed.

The MAIN PROGRAM then selects the appropriate display instructions. During a timed measurement or during an active sequence, the display may be blanked 276 until the activity is completed. If a blank 274 is indicated, the MAIN PROGRAM will simply return to the initial condition and display a series of dashed lines. If a blank 274 is not indicated, the MAIN PROGRAM will then call for the DISPLAY PROGRAM 270 to move the value of the selected function parameter to the display circuit.

PROCESS PROGRAM

Figure 8:
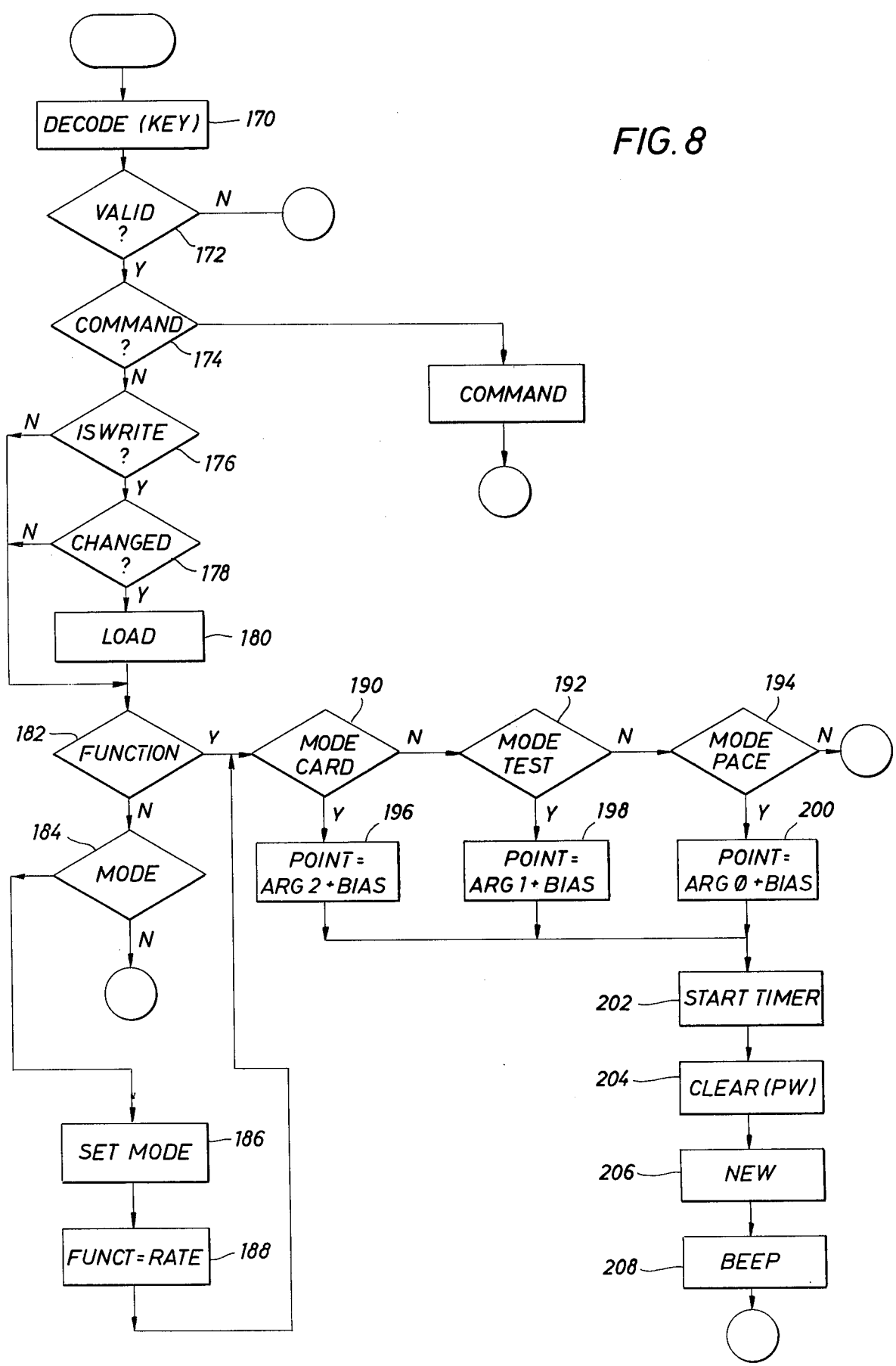
FIG. 8 is a flow diagram for the PROCESS program.

As hereinabove described, if the existence of a new and valid key is ascertained, the PROCESS ROUTINE is carried out to execute the appropriate request represented by the new key. The flow chart for the PROCESS ROUTINE is shown in FIG. 8. The input corresponding to the key is first examined and decoded 170 to ensure that a valid key is represented. If the key validity is not verified 172, the program is returned to the MAIN PROGRAM. If the key validity is verified 172, it is then determined whether the key requests that a command 174 be executed. If so, the COMMAND PROGRAM (see FIG. 9) is initiated to execute the command.

If a command 174 is not requested, the process program then determines whether a programmable function (ISWRITE) 176 is now present. If so, any changes 178 in the existing function are determined and loaded 180 into the system before any changes to the selected new function are made. If a programmable function 176 is not selected or if no change 178 has occurred, the PROCESS PROGRAM goes direct to further resetting of the operation.

The system then looks to see whether a new function 182 has been selected. If not, the selection of a new mode 184 is determined and the system sets 186 to accept a new mode, if selected. A determination of a new mode 184 automatically sets the function to the RATE function 188, a safe operating function regardless of the selected mode 186.

Once a new mode 184 is set, the PROCESS PROGRAM then returns to the mode selection verification routine. The selected input, new function 182 or new mode 186, is then compared with the selected mode 190, 192, or 194 to determine the memory address to access the program pointer which initializes the remainder of the program. Each operating state, i.e., mode, function, and command combination, is assigned a sixteen bit number which may conveniently be represented as four columns of four-bit numbers. Three of the columns are assigned to the selected modes, one to each mode. Each of the columns is referred to as an argument and each four-bit argument section contains a number which represents the position of the selected function in the selected mode group. In this manner, a memory location is accessed 196, 198 or 200 which sets the system conditions, as hereinafter described.

Thus, the PROCESS PROGRAM derives a particular argument as directed by the selected operating state. In a preferred embodiment, a memory table is accessed and the derived argument directs a pointer to address the beginning to each function routine. Each function is allotted eight bytes in the memory table, so that the location for the beginning of each function is determined by multiplying the argument value by eight. It is a peculiarity of the present system that eight must be subtracted from this result because the numbering was started at 1 rather than zero.

Each mode 190, 192, or 194 begins at a specified, or bias, location in this memory table and the final pointer value 196, 198, or 200, respectively, is obtained by adding the final argument value to the mode bias. The value of the pointer is loaded and the program initiated. The process program starts the system timers 202. A final check is made to determine whether the pulse width function has been selected and, if so, the timers are set to zero 204 since the timer outputs are convertible directly into pulse width.

The program now moves the eight bytes of new information 206 relating to the selected function and mode into the operating registers. In a preferred embodiment, the eight bytes contain the following information:

byte zero: location of decimal point in display, minimum function value, maximum function value;
byte one: write-enable flag, interrupt source, locations of nominal function value, and display increment for switch adjustable parameters;
byte two: lighted function lamps;
byte three: byte interrupt vector for service routine, vector for setting processors;
byte four: slave processor operation code to select a demand or fixed mode of pacing, margin test enablement, the selection of internal or external analog inputs for converting to digital values, and selection of the battery test;
byte six: alpha numeric display;
byte seven: not used.

Thus, the system is reset and enabled to operate in the new mode and function selected.

Finally, the preferred embodiment incorporates an audible indication that the system has been reset by providing a BEEP 208 program to produce the audible signal. This feedback is in addition to the visual display and is believed to be very useful in an operating room environment where the physician's attention must be focused on the patient as fully as possible. The program then returns to MAIN.

COMMAND PROGRAM

During the execution of the process routine, hereinabove discussed, it is determined whether the keyboard output indicates that a COMMAND has been entered. If so, the COMMAND routine is initiated to set the system operation in accordance with the operating parameters commanded by the depressed keys.

Figure 9:
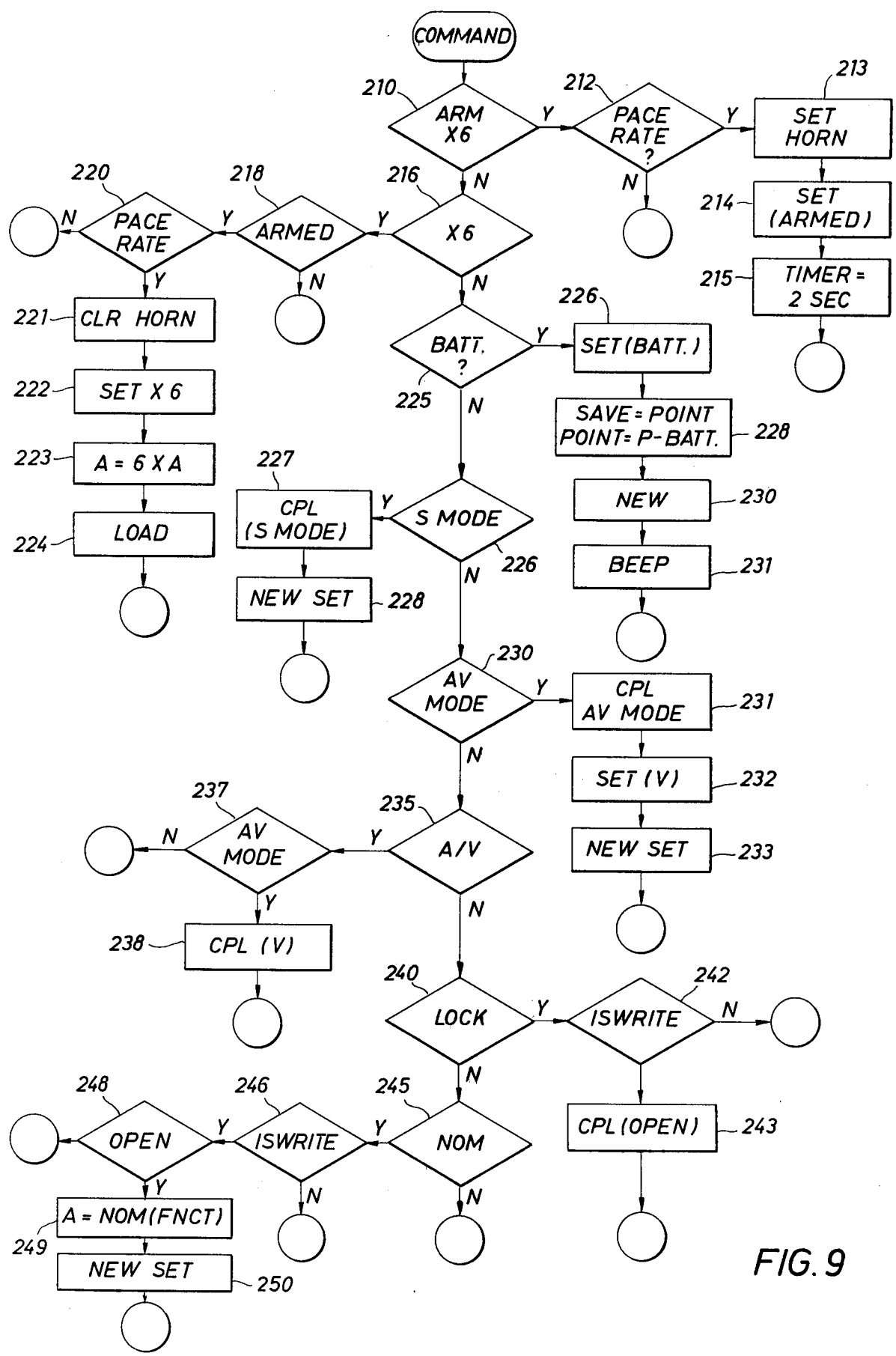
FIG. 9 is a flow diagram for the COMMAND program.

Referring now to FIG. 9, there is seen a COMMAND routine according to a preferred embodiment of the system. A first determination is whether the high frequency pacing rate, the "X6" key (108 in FIG. 1), is depressed to arm 210 the system. If so, the system also determines whether the pacer rate 212 key (85 in FIG. 1) is depressed. Both keys must be depressed simultaneously to set the system into the armed condition. An audible horn is set 213 and the system is armed 214. If both keys are not depressed, the routine is terminated. Once the system is armed 214, a two-second timer 215 is started and the routine returns to the main program. The next time COMMAND is executed the routine can determine whether the "X6" key (110 in FIG. 1) is now depressed 216 to start the high frequency pacing. The system affirms that the "X6" system is still armed 218, i.e., within the two-second period, and that the analyzer is still in the pacer RATE mode 220.

Once these determinations are affirmatively answered, the horn is disabled 221, the system is set to the "X6" condition 222, the pacing rate is set 223 at six times the display rate and loaded 224 into the operating register to control the system pacing output to the patient. It is apparent that this emergency routine is initiated only when the command keys are depressed in proper order and within a selected time to assure the routine is not inadvertently initiated.

Yet another command function is to test the battery voltage and, if that key (112 in FIG. 1) is depressed 225, the system is set 226 to a battery test condition, the program pointers then existing are set and saved 228, and the NEW routine 230 is selected to display the battery level.

Still another command is to establish 226 either a sensing or non-sensing mode. If the FIXED/DEMAND key (100 in FIG. 1) is depressed, the sensing mode bit is complemented 227 and the NEWSET routine 228 is initiated to update the display via the LAMP routine and to inform the slave processor that a sensing mode is in operation. The pacing output from the UPI is, thus, inhibited whenever a spontaneous heartbeat is sensed. By complementing 227 the sensing mode bit, the routine toggles between sensing and non-sensing on alternate depressions.

The COMMAND routine then determines 230 whether the A-V ON key (104 in FIG. 1) is pressed. If so, the appropriate data bit is complemented 231 and the system is set 232 to begin with a ventricular stimulating pulse. Again, the NEWSET routine 233 is initiated and the display and slave processor are informed and updated.

Next, the routine selects 235 the desired operating lead, the atrial or the ventricular, if any. If a selection has been made by depressing the ATR/VNTR key (106 in FIG. 1), the system determines whether the A-V mode 237 is also selected, since otherwise only the ventricular lead is available. If the A-V mode has been selected 237, the information bit is complemented 238 for the next pass through. The condition of the LOCK/UNLOCK key (103 in FIG. 1) is now checked 240 and, if depressed, the routine determines whether a programmable function 242 has been selected. If a programmable function has been selected, the appropriate register must be unlocked, so the open bit is complemented 243 and the register is set to obtain information from the switch.

The routine then determines whether the key (102 in FIG. 1) relating to nominal functions 245 is depressed. If not, the command routine is completed. If so, it is then determined whether a programmable function 246 is selected and, if so, whether the data register is open 248. If the data register is open, the nominal parameters are input 249 to the register and NEWSET 250 notifies the display and slave processor of the nominal values.

Thus, the COMMAND routine examines each of the possible command states and sets the analyzer to carry out the selected operating mode and function requested. Data bit complement steps are included in the sensing mode select 226, AV mode select 230, and programmable function determination 240 to toggle the routine on alternate depressions of the appropriate input keys. In addition, certain commands, such as the "X6" emergency operating command and the battery test command are carried to completion in the course of the routine. This ensures that the remainder of the analyzer routine is disenabled while these special commands are being executed.

SWITCH PROGRAM

Once the main program determines that a programmable function has been selected and the switch is unlocked, the SWITCH program is activated. The purpose of the SWITCH program is to determine whether the input from the switch has changed since the last program cycle and to determine whether the change is upscale or downscale, and to set new function values for the system. The program is designed to verify the change before any value is changed.

Figure 10:
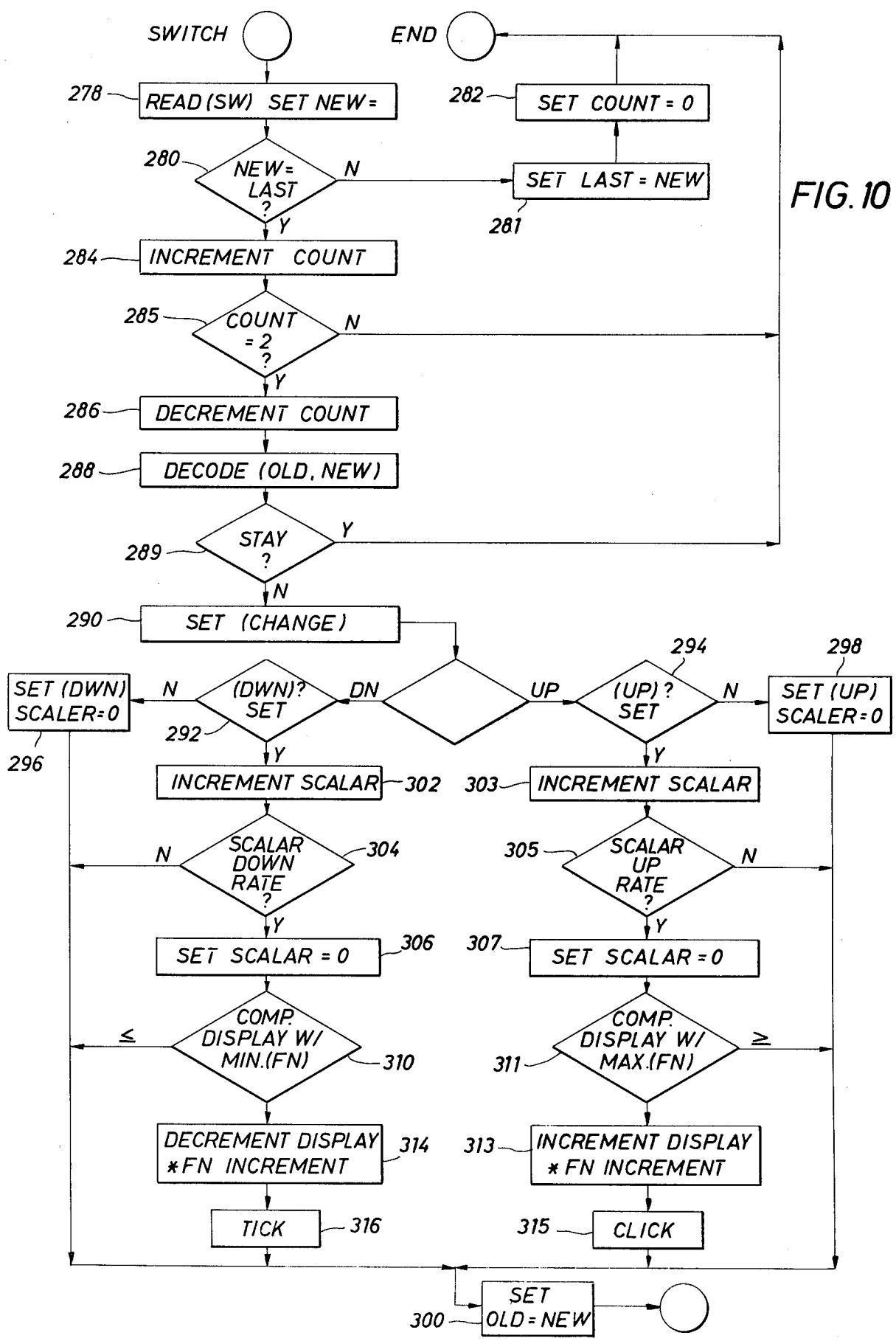
FIG. 10 is a flow diagram for the SWITCH program.

Referring now to FIG. 10, there may be seen a flow diagram depicting the switch program. The switch setting is read 278 and the program sets the read switch value as the new program value. The value is compared 280 with the previously stored switch value and, if a change has occurred, the reading is verified by setting 281 the last reading to the new reading, resetting an internal count to zero 282, as hereinafter explained, and again reading the switch. Now, if the new switch reading is the same as the last switch reading, the internal program count is incremented by one 284 on the next cycle. If the count is not yet two (2) 285, the entire sequence is repeated to again verify the switch reading. If no change has occurred, the count will now be two (2) and the count will be decremented by one (1) 286 and the switch reading passed to the decoding step 288.

In a preferred program decoding 288, a conventional two-bit grey code is used to obtain a number for further processing. Thus, a four-bit number is formed, using two bits representing the old number and two bits representing the new number. The combination uniquely determines the relative scale relationship of the two numbers. Since an optical switch may be employed, the new number may equal the old number, in which case a stay is determined 289 and the program is returned to its initial condition. If no stay is set, then a change is set 290 and the decoded number is passed to the scaling portion of the program.

The decoded number is examined 291 to determine whether the indicated scale direction has already been set 292 or 294. If not, the scale direction is set in the indicated direction, down 296 or up 298, and the old number is set 300 to the new number and the program is initialized. A new decoded number is then obtained from further rotation of the switch in the indicated direction and the new number is now processed in the indicated scale direction on a subsequent program cycle. It should be noted that this action prevents a momentary turn in the wrong direction from changing the system, i.e., a hysteresis is introduced and two program cycles are required to reverse the system direction.

Once the direction is established 292 or 294, the scaler is now incremented by a single unit 302 or 303, respectively. The program then determines 304 or 305 whether the total number of scaler increments is now equal to a preset number of increments which would equal an increment in the display value. If the selected number of increments has not yet been obtained, the program returns to obtain another incrementing cycle until the preselected number of increments has been collected.

At that time, the incremental scaler is set to zero 306 or 307 and the program then compares 310 or 311 the present function value with the minimum or maximum values, respectively, for the selected function, as obtained from the function memory library during the PROCESS program set up. If a maximum or minimum has been exceeded, the display is not changed and a new program cycle is initiated.

If the function is within the selected bounds, then the function value is either incremented 313 or decremented 314, depending on whether the change is up scale or down scale, respectively. The display change corresponding to one display increment is also determined from the function memory library during the PROCESS program and that value is now applied to the existing display.

In a preferred embodiment, an audible signal is also provided to assist the attending physician in mainpulating the switch. The audible signal may be further modified to provide a "click" 315 for an upscale change and a "tick" 316 for a downscale change. It has been found that these audible signals greatly assist in smoothly arriving at the desired value. Further fine adjustments can be made by reference to the audible signals without diverting attention to the visual output. Following the incremental change, the system is set to repeat the cycle and the cycle continues as the MAIN program repeats its cycle.

Thus, the optical switch acts to progressively increment or decrement the displayed function value as the switch dial is rotated. Although no specific arcuate rotation is associated with a single incremental change, the frequency of program repetition generally acts to provide a steadily changing value as the dial is rotated. The audible signal assists in maintaining a steady dial rotation at a suitable angular rate. The various program checks and recycles assist in obtaining an incremental change only when there is no ambiguity in any of the program inputs.

NO PACE PROGRAM

There are instances in which the system is simply gathering data for processing. During this time the active portions of the system are not utilized and sensed data is received and stored. The sensing activities generally occur during various cardiac test mode operations such as heart rate, heart beat interval, and voltage output determination, and when data is being collected for the Margin routine, hereinafter discussed.

Figure 11:
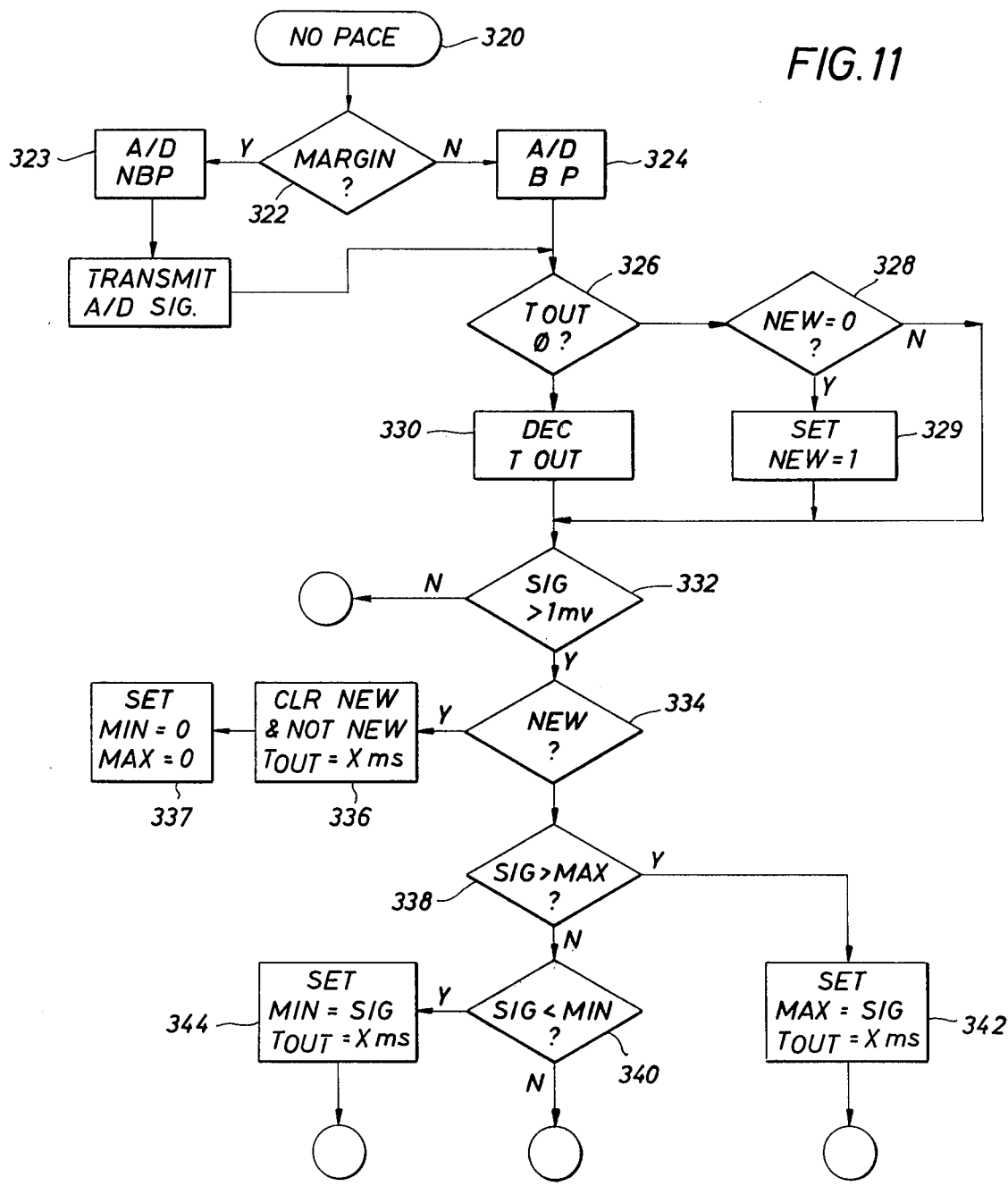
FIG. 11 is a flow diagram for the NO PACE program.

Accordingly, when the NO PACE routine FIG. 11 is selected, the routine first determines whether the MARGIN function 322 is selected. Where the margin function is selected, the data is obtained without passing the input through a band pass filter and the unfiltered signal is converted to a digital signal 323. Where other operating parameters are being monitored, the incoming signal is passed through a bandpass filter, as hereinafter described, and converted to a digital signal 324.

If a new time period is being established 326, i.e., time out is now zero, and a new function has been selected 328, the system issues a communicating pulse 329 on the communications link to signal the master processor that data collection is beginning. If a measuring interval has already begun, the timer is decremented 330 and the incoming signal level is monitored 332. If the signal is less than a threshold value, which may conveniently be less than 1 mv, the program returns to an initial condition. If the signal is greater than the selected threshold, i.e., greater than 1 mv, the system again checks 334 to see if this is a new function selection. If so, the registers are cleared and the timer is set to a selected timing interval, which may conveniently be 200 ms. The registers storing the minimum and maximum function values are set to zero 337 and the time out set to one. The routine is then initialized. On the next cycle, the time out is now zero but this is not a new function so signal strength is again checked and, if adequate, the system begins to make the maximum and minimum determinations.

During each cycle, the incoming signal is compared with maximum 338 and minimum 340 values stored in the system an the values updated 342 and 344 based on the results of the comparison. Each time a new minimum 344 or maximum 342 value is determined, the timer is reset and the routine initialized. The routine continues until no new maximum 338 or minimum 340 has been found during the selected timing interval of 200 ms.

Thus, maximum and minimum values are routinely available and the time during which a new maximum or minimum has not been found is also available. It is apparent that this data can be processed to determine the various cardiac operating parameters relating to heart rate, heartbeat interval, and maximum cardiac output voltage. As hereinafter explained, the timed data can be collected and stored to obtain a stored representation of an actual cardiac heartbeat.

AVERAGE CURRENT DETERMINATION

One operating characteristic of considerable interest is the average current delivered by the internal pacer when an output pulse is produced to stimulate the patient. The average current required during a given pulse is, in turn, a function of both the output voltage and the pulse width. Referring to FIG. 4, a voltage signal is produced across resistor R3 to form a signal proportional to the delivered current.

In one approach, the voltage signal across R3, which is related to the delivered current, is integrated over the duration, or width, of the pulse. This integrated value, when divided by the pulse width, provides an output signal which is proportional to the average current during the pulse. Operational amplifiers may be conventionally designed to operate as integrators, where the maximum output signal is related to an internal reference voltage.

As hereinabove explained, the pacer analyzer depends on a local battery source for power, where the battery source has a given output voltage available. Thus, an integrator circuit must operate within the constraints of the local battery voltage, or a suitable reference voltage which is not higher than the internal battery voltage.

It is desirable, however, to provide a range of pulse widths, a typical range being from 0.05 msec. to 3.0 msec., a range of 60:1. Assuming that a 3.0 volt reference voltage is selected and it is desired to produce a pulse width in 0.05 msec. increments, it will be readily apparent that each incremental increase in pulse width would produce only a 0.05 volt change in the integrated current. It is very desirable to increase the overall system sensitivity above the 0.050 volt unit pulse width.

As hereinafter explained, the present system includes a bifurcated approach to increase the system sensitivity at both the low ranges and the high ranges. A break point is selected which tends to maximize the sensitivity over each of the ranges.

In a preferred embodiment of the present invention, the sensitivity in the low range is increased by using a relatively high, fixed system gain to produce a relatively steep slope of the integrated output as a function of pulse width. The sensitivity in the high range is increased by varying the gain constant as a function of pulse width to produce a constant maximum integrated output for each pulse width. The operation of the system and the circuit components forming the average current determining circuitry may be seen in FIG. 12.

An digital-to-analog converter (DAC) 346 is arranged as a divider circuit, where the digital input N 348 acts to set the overall gain of multiplying DAC 346.

Figure 12:
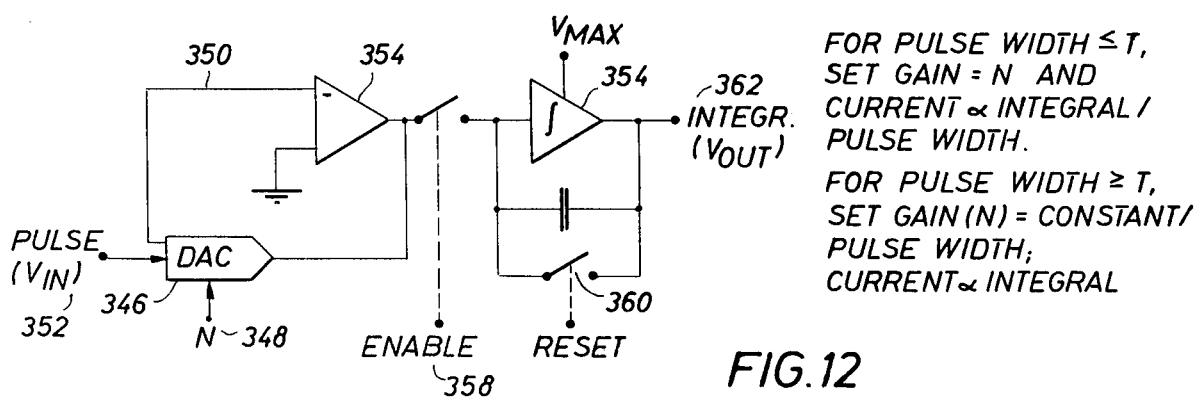
FIG. 12 is a schematic of an average current determining circuit.

As depicted in FIG. 12, DAC 346 is connected as a divider circuit where the output voltage 350 equals the input voltage 352 divided by the digital input number N 348. Operational amplifier 354 is part of the divider configuration. Output voltage 350 is then directed to a conventional integrator circuit using operational amplifier 355 to produce the INTEGRAL signal. The operation of the integrator circuit is further controlled by analog switches 358 and 360, as hereinafter discussed, which permit integration generally only during the duration of the pulse to minimize system drift.

Thus, the analog switch 358 enables the integrating circuitry and switch 360 opens, stopping the continuous reset of the integrator, just prior to the introduction of a pulse into the system. Switch 358 remains enabled until the pulse is completed. The INTEGRAL signal 362 (FIG. 3, signal U) is subsequently presented to a multiplexer, converted to a digital signal and processed by the microprocessor circuitry to obtain the average current (see FIG. 3). Switch 360 is again closed to reset integrator 354.

Figure 13:
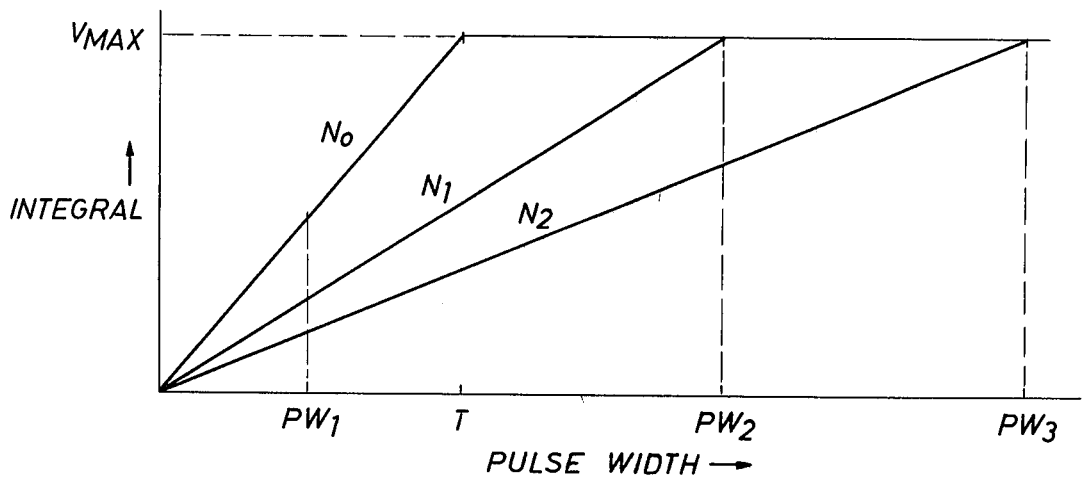
FIG. 13 is a graph showing the operating characteristics of the average current circuit depicted in FIG. 12.

The operation of the integrating circuitry in cooperation with the signal processing is depicted by reference to FIG. 13. FIG. 13 shows the integrated output as a function of pulse width in the low and the high ranges, where pulse width T is the break point. Thus, the system gain $N_O$ is constant for pulse widths up to a pulse width T. The break pulse width T is selected to yield a slope which produces satisfactory sensitivity in the low range of pulse widths for a selected incremental pulse width unit. Without a break point, the small pulse width signal would be too sensitive to noise and op-amp variations to be reliable. In this range, the average current is proportional to INTEGRAL/PULSE WIDTH.

When the pulse width exceeds the break value T, the processing circuit determines that the pulse width is greater than the break value T and sets the system gain to be a function of pulse width to obtain the maximum output from the integrator 350 (FIG. 12). Typical operating lines are shown in FIG. 13 as lines $N_1$ and $N_2$ for pulse width $PW_2$ and $PW_3$, respectively. Now the average current is only proportional to the integrated output signal, INTEGRAL. This may be converted directly into an average current output reading.

Thus, the system design acts to accommodate a wide range of pulse widths and spacing between pulses. The average current of each pulse is obtained and the system is disenabled between pulses to prevent system drift. System sensitivity is increased at the low range by using a constant, relatively high gain to obtain large changes in the integrated output for a small change in input. At the high range, a constant output is provided within the system constraints where the system gain is controlled and the integrated output is used as a direct indication of the average current.

Referring again to FIG. 13, there may be illustrated various operating characteristics of the operation of the average current determining apparatus as a function of various break points, T. Thus, at the smallest available break point, i.e., the first increment of 0.05 msec., only gain control is used to determine average current. At the other extreme, where T is 3.0 msec., only a constant gain is employed. In a preferred embodiment, a T of 1.0 msec. has been selected as the break pulse width. It should be noted that a variety of acceptable pulse widths may be selected for the break point, although pulse widths below about 0.25 msec. are generally not desirable because of the large gain factors which are required. Since the gain is represented by a digital number, it may be generally determined with a high degree of accuracy to produce the requisite overall system resolution.

MARGIN TEST

A particular feature of the subject pacer system analyzer is the capability of determining the performance of the patient's pacer in response to the patient's heart characteristics without connecting the patient's pacer to the patient. As hereinbelow described, this is accomplished by detecting and storing one complete heartbeat from the patient and thereafter re-creating that heartbeat with variable amplitude. The re-created heartbeat is presented to the patient's pacer until a threshold amplitude is reached where the patient's pacer no longer responds. A safety margin value can then be determined based on the amplitude of a normal heartbeat from a patient and the threshold amplitude determined from the margin test. As hereinabove described, the test wave, or haversine wave, generated by the pacer system analyzer is not determinative of pacer performance because of the many frequency characteristics of an actual heartbeat which greatly change the waveform after passage through conventional pacer filter circuitry.

MARGIN ROUTINE

Figure 14:
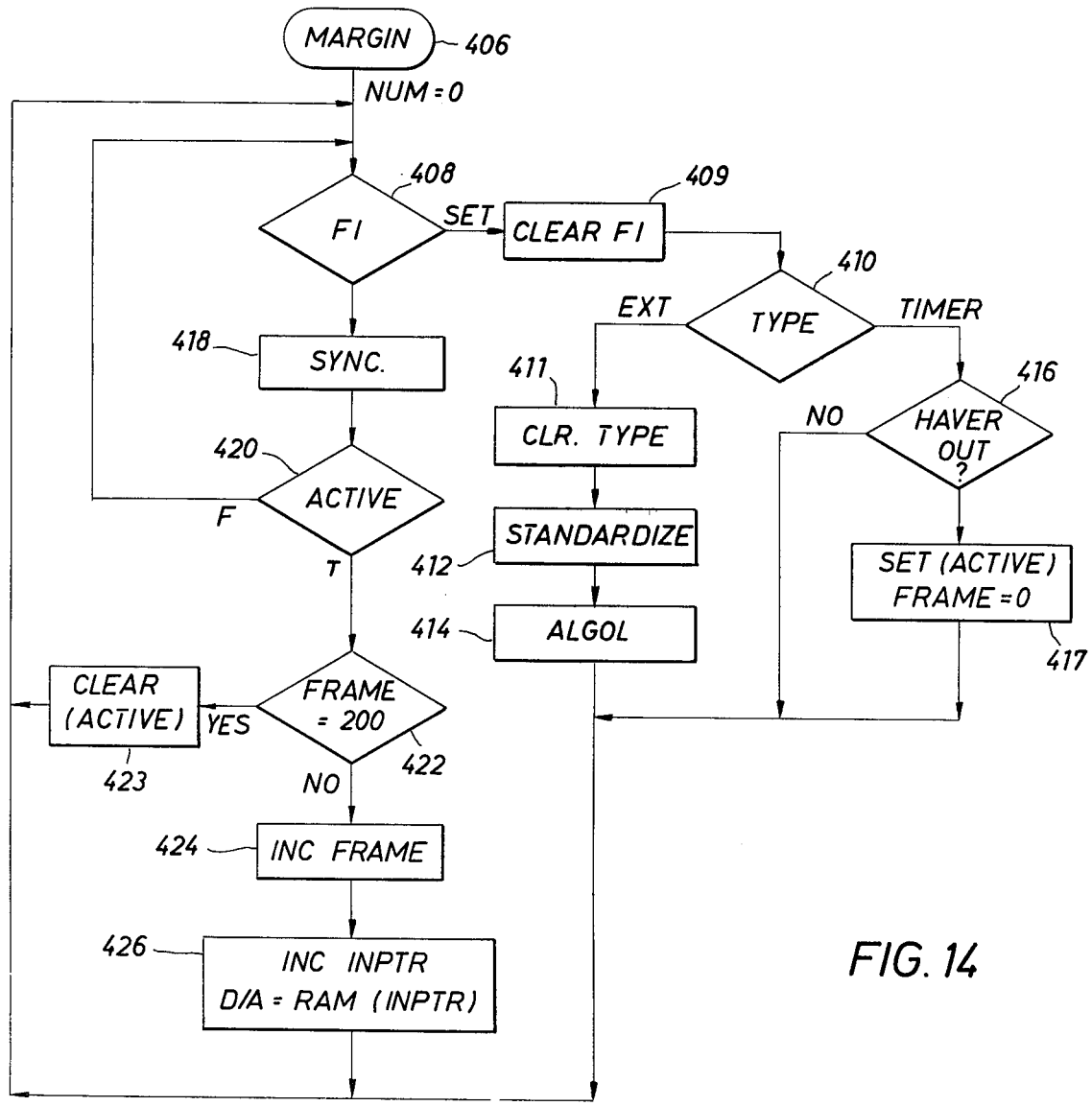
FIG. 14 is a flow diagram for the MARGIN program.

Referring now to FIG. 14, there may be seen the operating routine for the pacer system analyzer during the margin test. The margin test is initialized by depressing the margin key (96 in FIG. 1) while in the Heart Measure 83 mode (see FIG. 1). The Margin key 96 must remain depressed throughout the margin test. Thus, MARGIN routine 406 is initialized and the system counter set to 0.

On the first operating cycle, a flag 408 is detected. The flag is cleared 409 and the flag type 410 is determined. On this first cycle, the flag is set as an external type, indicating the occurrence of a pacer pulse. The flag type is cleared 411 and the routine then standardizes 412 the signal to be input to the pacer. The standardization operation 412 sets the ending level of the previous output wave to the starting level of that wave, if necessary, and resets the input pointer to the proper storage frame location, as hereinafter described. On the first cycle, however, there is not yet a stored wave for use.

Referring still to the first cycle, the MARGIN routine then initiates TRY $\phi$ of an iterative routine ALGOL 414. ALGOL 414 increments a Try counter during each program cycle, as hereinafter described for FIG. 15. At TRY $\phi$ 428, the FINDER program 430 is initialized to find and store a suitable wave form. The ALGOL 414 and FINDER 430 routines are more particularly described with respect to FIGS. 15 and 16, respectively.

Once a suitable wave has been detected and stored, the system recycles to flag 408. If no flag is set, the system waits for about 2.65 msec. to synchronize the cycle with the opeating routine of the slave processor UPI. Following SYNC 418, an Active 420 determination is made, i.e., is a stored waveform being produced for the patient pacer? If not, the routine recycles to flag 408.

To initiate the beginning of a Margin test, a timer first sets a flag 408 that it is time to play out a stored waveform. The flag is cleared 409 and the type 410 determination shows that a timer flag has occurred. Once the proper number of timer interrupts have occurred, a waveform output determination 416 becomes affirmative and the system is set 417 into an active condition and the frame counter is set to zero, i.e., the beginning of a stored wave. After the system is set, the cycle returns to the active 420 query. At this time, the query is affirmative and a frame output cycle begins. Frame count 422 maintains the frame output for 200 frames. At each frame, the frame counter is incremented 424 and the actual memory location pointer 426 is incremented to move the next frame value from a stored location for converting to an analog signal and presentation to the patient pacer.

It should be noted that re-creating the patient's heartbeat is done using the internal circuitry used to generate the haversine test signal. Thus, the stored value obtained by the input pointer is used to control DAC 34 (FIG. 3) to reproduce the desired wave shape and the amplitude of the wave shape is determined by DAC 32 (FIG. 3), as controlled by the ALGOL 414 program.

The 200 stored frames of heartbeat data are used to form a signal, which is presented to the patient pacer. Once the 200 frames have been presented, the frame count determination 422 is affirmative and the Active signal is cleared 423. The Margin routine then returns to normal cycling.

Figure 15:
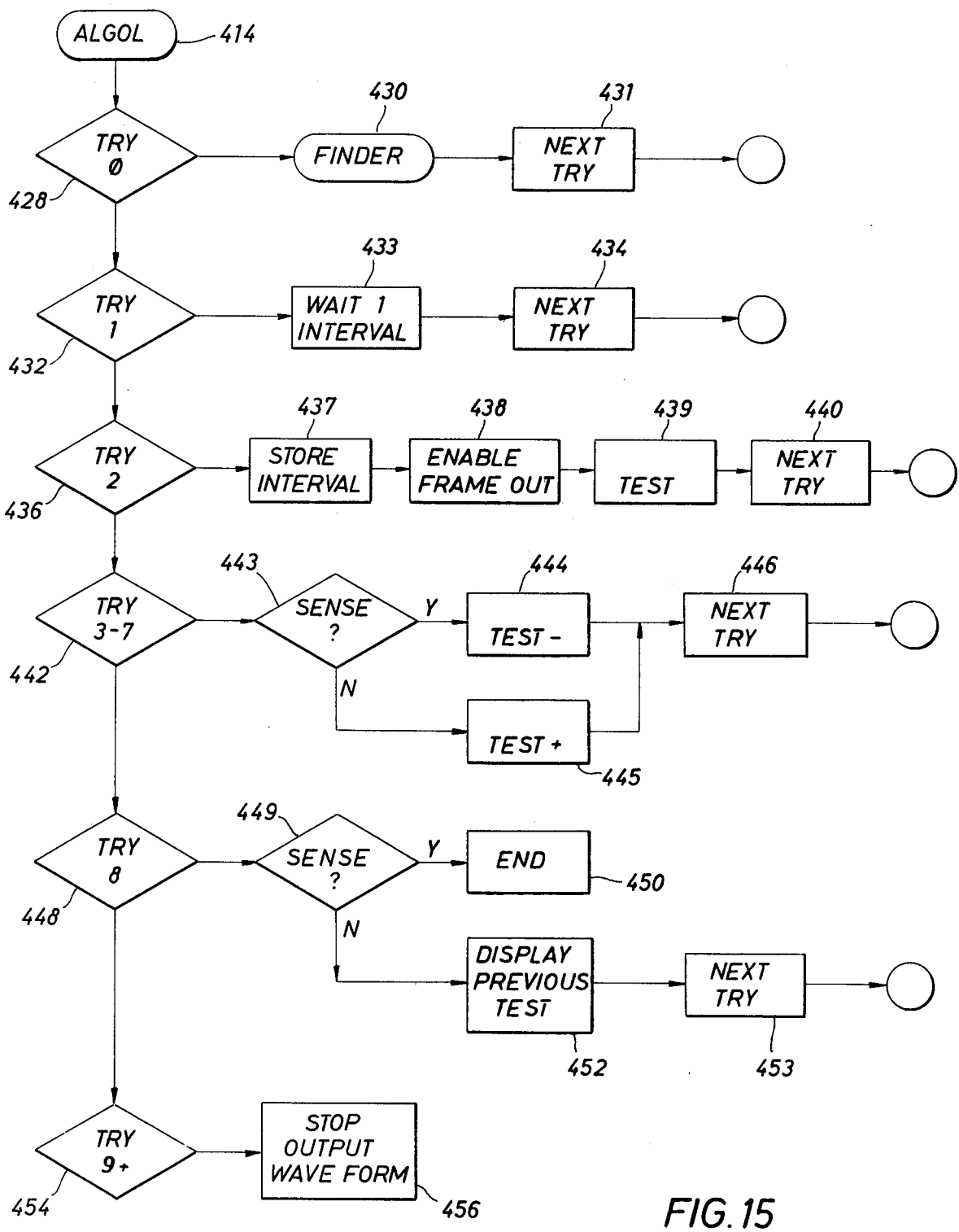
FIG. 15 is a flow diagram for the ALGOL program.

The ALGOL routine is used to determine the threshold value of the pacer for detecting a patient's heartbeat wave. A suitable operating routine is shown in FIG. 15. As hereinabove discussed, TRY $\phi$ 428 is used to initiate the FINDER 430 program. On the next cycle TRY-1 432, the system waits 433 one interval and sets the NEXT TRY 434. At TRY-2 436, the test interval is stored 437 and the frame outputs are enabled 438. A first test amplitude is tried 439 and the system is incremented 440 for the NEXT TRY.

At TRY-3 through TRY-7 442, the response of the patient pacer to the trial heartbeat is sensed 443. If a patient pacer output pulse is sensed, the test value is incremented 444. If no output pulse is sensed, the test value is decremented 445. The incremental changes to the test values at each one of TRY-3 to TRY-7 are selected to converge the routine to a preselected accuracy. In one embodiment the initial test wave amplitude is set at 50% of the original *actual* amplitude. The first incremental change is plus or minus 25% from the original amplitude and each succeeding trial change is about one-half the previous trial change. Thus, the incremental changes are progressively smaller as the routine converges.

At TRY-8 448, the routine senses 449 the pacer response to the last input waveform. If a response is obtained, the program is terminated 450 without displaying a result. If no response is obtained, the system has successfully converged and the previous test result is displayed 452 and the system goes to the NEXT TRY 453. At TRY-9 454, the waveform output is terminated 456.

Thus, in operation, the Margin test acts to find and store a representation of an actual output heartbeat from the patient, as hereinafter described. The routine then sets a timer so that an output pulse is presented to the patient pacer at an interval which is outside the pacer refractory period. After each timer flag, the ALGOL program sets the amplitude for the wave and initiates a frame output to the pacer at the selected amplitude and the regular program then reproduces a signal for the patient pacer having waveform characteristics functionally related to the actual patient heartbeat waveform. The response of the patient pacer is sensed after each waveform is presented and a new trial amplitude selected based on the results of the sense test. A threshold value is determined and a sensitivity is calculated and displayed.

Figure 16:
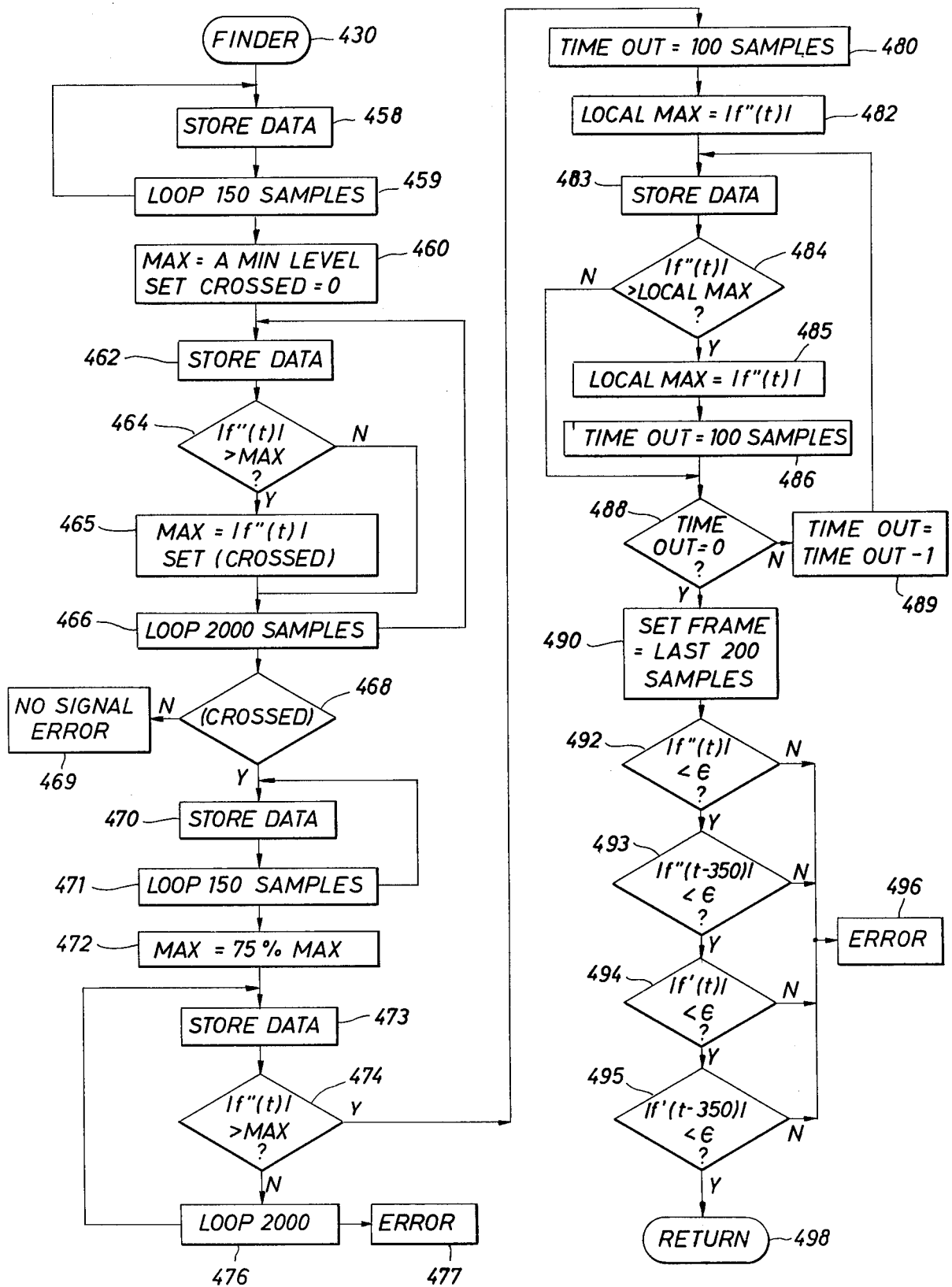
FIG. 16 is a flow diagram for the FINDER program.

Referring now to FIG. 16, there is depicted an operating routine FINDER 430 for selecting and storing a complete representation of a patient's heartbeat waveform. The pacer system analyzer is generally producing pacer output pulses to the patient throughout the Margin routine. However, during the FINDER routine, no output pulses are provided in order to insure that the heartbeat waveform which is selected and stored is that waveform produced without any external stimulation.

Thus, FINDER 430 is initiated during TRY-$\phi$ of the ALGOL routine. A selected number of storage locations are allotted to the program and data is accumulated sequentially in the storage locations on a first-in, first-out basis. Thus, data is continually being placed at a location corresponding to frame zero and moved sequentially through the storage location to a final location corresponding to frame 200. The routine first begins to store data 458 and a loop counter 459 cycles for a time sufficient to obtain normal waveform characteristics from the heart. In a preferred embodiment, about 300 msec., representing about 150 samples, is sufficient.

The routine next acts to store data representative of a typical heartbeat and to detect various characteristics of that typical heartbeat. The routine SETS 460 a first threshold value MAX to a preselected minimum level and a crossing counter to zero. The routine continues to store data 462 and the second derivative of the incoming waveform is computed and compared 464 with the set MAX. The second derivative is selected because a maximum value for the second derivative generally occurs at a peak location in the waveform. If the computed second derivative during each cycle is greater than the set MAX, then MAX is reset 465 to the value of that second derivative and the crossing counter is incremented. If the second derivative is not greater than the set MAX, the routine just returns to the loop counter 466.

A large number of samples, preferably about 2000, are analyzed. At the end of the loop count, the crossing detector is sampled 468 to verify that at least one value of MAX has been obtained greater than the preselected minimum level. If no crossing has occurred, an ERROR signal 469 is entered. If a crossing has occurred, the system continues to store data 470 and enters a 150 sample data loop 471 to clear the peak data from the storage register.

Now, the test value MAX is set 472 at 75% of the value of MAX obtained during the 2000 loop sampling. The routine again stores data 473 and begins a new peak determination by computing the second derivative of the incoming wave form for comparing against the set MAX. This comparison continues until loop counter 476 reaches 2000 or until the new second derivative exceeds the set MAX. If a new MAX is not detected 474, the routine ends in an ERROR 477.

As soon as a new MAX is detected 474, a local time out counter is set 480 to 100. A local MAX is set 482 to the value of the second derivative being computed at 482. The system again stores data 483 and continues to compute the second derivative for comparison 484 with the set local MAX. If the local MAX is not exceeded, the count is compared with zero 488 and, if not zero, the counter is decremented 489 one count and returned to the data frame 483. Once a second derivative is detected which exceeds the set local MAX, local MAX is reset 485 to the larger second derivative and the time out is reset 486 for another one hundred samples. Thus, local MAX is continually updated to the largest detected value of the second derivative until a new local MAX has not been found for one hundred samples.

After one hundred samples without a new local MAX, time out is now zero 488. This means that the detected peak has advanced in the storage register for one hundred frames. This criteria establishes that a complete wave form is now in the storage register and the program sets a complete frame 490 embracing the last two hundred samples.

The routine now acts to check the stored waveform to verify that it has characteristics compatible with the waveform from a completed heartbeat. In the particular embodiment, 200 samples is equivalent to a time of 400 msec. The program checks both the second derivative and the first derivative near the beginning of the frame and the end of the frame to verify that the stored waveform is generally smooth and generally level.

Thus, if (t) represents a time near the end of the stored waveform and (t-350) represents a time near the beginning of the waveform, the second derivative is Compared 492 and 493, respectively, at each of these times with a preselected maximum error value. The first derivative is then computed at each of these times and Compared 494 and 495, respectively, with a preselected maximum error. Exceeding the preselected maximum error in any of these tests causes an ERROR signal 496. If all of the tests are successful, the FINDER routine is completed and the routine returns 498 to the main program. Thus, a complete waveform is stored and 200 frames of data are available for re-creating a complete waveform for the margin test.

Thus, it is readily apparent that the margin test provides a useful and additional verification that the patient pacer is fully compatible with the patient prior to actually connecting the pacer to the patient. Further, a margin value is computed which provides further information on the degree of compatibility between the pacer and the patient. This information could not heretofore be obtained and the final verification required that the pacer actually be connected to the patient. Even then, it could only be verified that the pacer sensed the actual heartbeat waveforms produced by the patient and there was no way to determine the degree to which the pacer was operating near a threshold level.

It is therefore apparent that the present invention is one well adapted to attain all of the various features hereinabove set forth, together with other features which will become obvious and inherent from a description of the apparatus itself. It will be understood that certain combinations and subcombinations are of utility and may be employed without reference to other features and subcombinations. This is contemplated by and is within the scope of the present invention.

What is claimed is:

1. An analyzer apparatus connected to a heart and an implantable pacer for monitoring the operational parameters of signals generated by the heart and the implantable pacer and for testing the pacing operation of the pacer, said apparatus comprising:

a sensing circuit for sensing the operational parameters of the signals of the heart;

a pacer operating circuit for generating a simulated heart signal to the implantable pacer and for sensing the operational parameters of signals of the implantable pacer;

a heart stimulating circuit for generating stimulation signals to pace said heart;

control means for determining which operational parameters of the heart and pacer signals are monitored and for selecting parameter values for the signals generated by said pacer operating circuit and heart stimulating circuit;

enabling processing means for activating said heart stimulating circuit to pace the heart and monitoring and generating digital representations of the sensed heart and pacer signals and the signals generated by the heart stimulating circuit;

supervising processing means responsive to said control means for controlling the enabling processing means and for receiving said transmitted digital representations;

said supervising processing means responsive to said enabling processing means, for controlling the operation of the heart stimulating circuit by transmitting the parameter values selected by the control means to said enabling processing means; and display means, responsive to said supervising processing means, for displaying said digital representations and the parameter values selected by said control means.

2. The analyzer apparatus of claim 1, wherein said control means includes:

a plurality of parameter selection means, each selection means for generating a code indicating its manual activation; and a moveable value adjust control for generating signals corresponding to the direction of its movement;

said supervising processing means including programmed means for generating an initial parameter value and for modifying said value by to a desired magnitude by predetermined increments within a predetermined range in response to movement of said value adjust control, said initial value, range and increments being determined by the code of each activated control means.

3. The analyzer apparatus of claim 2 wherein each parameter selection means includes a pushbutton switch.

4. The analyzer apparatus of claim 1 or 2, wherein the enabling processing means includes a signal multiplexing means for selecting a signal from a plurality of signals monitored by the enabling processing means, and converter means responsive to said supervising processing means, for generating a digital representation of said selected signal.

5. The analyzer apparatus of claim 1 or 2 wherein said supervising processing means includes a programmable microprocessor and programming instructions for controlling the operation of said microprocessor.

6. The analyzer apparatus of claim 5 wherein said supervising processing means further includes memory means for storing said parameter values and said programming instructions.

7. The analyzer apparatus of claim 6 wherein said memory means includes a random access memory.

8. The analyzer apparatus of claim 7 wherein said memory means further includes a read only memory.

9. The analyzer apparatus of claim 1 or 2 wherein said pacer operating circuit includes:
  haversine generating means for generating a simulated heart signal having a haversine waveform;
  signal output indicator means for indicating the presence of signals generated by the pacer; and
  a peak detector circuit for generating a signal proportional to the peak voltage of said signals of the pacer.

10. The analyzer apparatus of claim 9 wherein said haversine generating means comprises:
  a reference signal generator for producing a fixed reference signal;
  a first multiplying digital-to-analog converter connected to the output of said reference signal generator and responsive to the supervising processing means for generating a variable reference signal, said variable reference signal being a multiple of the fixed reference signal; and
  a second multiplying digital-to-analog converter, responsive to the supervising processing means, for producing a haversine signal of varying rate, said second digital-to-analog converter further responsive to said variable reference signal for varying the amplitude of said haversine signal.

11. The analyzer apparatus of claim 9 wherein the signal output indicator means is a Schmitt trigger.

12. In the analyzer apparatus of claim 2:
  the control means includes a plurality of indicator lamps; and
  the enabling processing means includes means, responsive to the manual activation of one of said parameter selection means, for selectively illuminating at least one of said lamps to provide visual feedback of said activation.

13. The analyzer apparatus of claim 2 wherein the supervising processing means further includes:
  programmed means for computing a multiplier value proportional to said desired magnitude;
  means for applying said multiplier value to said heart stimulation circuit and pacer operating circuit to define the magnitude of output signals generated by the circuits; and
  means for selectively activating the heart stimulation circuit and pacer operating circuit.

14. The analyzer apparatus of claim 1 wherein said enabling processing means includes output expander means, responsive to the supervising processing means, for generating control signals to selectively activate the sensing circuit or the heart stimulating circuit.

15. The analyzer apparatus of claim 1 wherein the heart stimulating circuit includes an atrial stimulation circuit and a ventricular stimulation circuit, each responsive to said enabling processing means, for respectively selectively stimulating the atrium or ventricle of the heart.

16. The analyzer apparatus of claim 1 wherein the sensing circuit includes:
  average current measuring means for generating a signal proportional to the average current generated by said heart stimulating circuit; and
  filter means, having a predetermined frequency range, for transmitting an output signal proportional to the sensed signals of the heart when the frequency of said sensed signals is within said frequency range and for rejecting said sensed signals when the frequency of the signals is outside of said frequency range.

17. The analyzer apparatus of claim 16 wherein said filter means includes a bandpass filter having a frequency range substantially similar to the frequency range of said implantable pacer.

18. An analyzer apparatus connected to a heart and an implantable pacer for monitoring the operation of the heart and the pacer and for testing the pacing operation of the pacer, the apparatus comprising:
  first circuit means for generating a simulated heart signal to the pacer and for receiving electrical impulses from the pacer;
  second circuit means for receiving electrical impulses from the heart;
  third circuit means for producing and delivering electrical stimulating pulses to pace the heart;
  input means for generating command signals;
  an adjustment means for generating an adjustment signal;
  first digital processor means, responsive to said command signals, for generating a first control signal for selectively activating one of said first or second circuit means, and for generating a second control signal;
  said first processor means, responsive to the adjustment and command signals, for generating values representing desired levels of output of said first, second, and third circuit means and for transmitting the generated values to the respective circuit means;
  second digital processor means for generating at least one timing signal and, responsive to the second control signal, for selecting and transmitting to the first digital processor means, a digital value proportional to one of the received heart or pacer impulses;
  said second digital processor means for controlling the rate and pulse width of the electrical impulses produced by said third circuit means, a signal corresponding to the magnitude of said rate and pulse width being generated by said first digital processor means and applied to said second digital processor means in response to the timing signal generated by said second processor means; and
  display means, responsive to said first digital processor means, for displaying the digital value transmitted by the second processor means.

19. The analyzer apparatus of claim 18 wherein the first digital processor means includes a programmable microprocessor and programming instructions for controlling the operation of the microprocessor, and memory means for storing said programming instructions and the values representing said desired levels of output of the circuit means.

20. The analyzer apparatus of claim 19 wherein said memory means includes a random access memory.

21. The analyzer apparatus of claim 20 wherein said memory means further includes a read only memory.

22. The analyzer apparatus of claim 18 wherein said second digital processor means includes:
  a programmable microprocessor and programming instructions for controlling said microprocessor;
  an output expanding means for selectively activating the second or third circuit means;
  a signal multiplexing means for selecting a signal from a plurality of heart and pacer impulse signals; and
  converter means responsive to said first digital processor means for generating a digital representation of said selected signal.

23. The analyzer apparatus of claim 18 wherein the third circuit means includes an atrial stimulation circuit and a ventricular stimulation circuit, each responsive to the second digital processor means, for respectively selectively stimulating the atrium or ventricle of the heart.

24. The analyzer apparatus of claim 18 wherein the second circuit means includes:
average current measuring means for generating a signal proportional to the average current generated by said third circuit means; and
filter means, having a predetermined frequency range, for transmitting a signal proportional to the received heart impulses when the frequency of said impulses is within said frequency range and for rejecting said impulses when the frequency of said impulses is outside of said range.

25. The analyzer apparatus of claim 24 wherein the filter means is a bandpass filter having a frequency range substantially similar to the frequency range of said pacer.

26. The analyzer apparatus of claim 18 wherein said first circuit means includes:
haversine generating means for generating a simulated heart signal having a haversine waveform;
signal output indicator means for indicating the presence of impulses from the pacer; and
a peak indicator circuit for generating a signal proportional to the peak voltage of the pacer impulses.

27. The analyzer apparatus of claim 26 wherein said haversine generating means comprises:
a reference signal generator for producing a fixed reference signal;
a first multiplying digital-to-analog converter connected to the output of said reference signal generator and responsive to the first digital processor means for generating a variable reference signal, said variable reference signal being a multiple of the fixed reference signal;
a second multiplying digital-to-analog converter, responsive to the first digital processor means, for producing a haversine signal of varying rate, said second digital-to-analog converter, responsive to said variable reference, signal for varying the amplitude of said haversine signal.

28. The analyzer apparatus of claim 26 wherein the signal output indicator means is a Schmitt trigger.

29. In the analyzer apparatus of claim 18:
said input means includes a plurality of indicator lamps; and
said second digital processor means includes means, responsive to said control signals and said first digital processor means, for selectively illuminating at least one of said indicator lamps to provide visual feedback of said control signal generation.

30. An analyzer apparatus connected to a heart and an implantable heart pacer for monitoring the operation of the heart and the pacer and for testing the pacing operation of the pacer, said apparatus comprising:
a sensing circuit for monitoring electrical signals from the heart;
a pacer operating circuit having adjustable operating parameters for generating a simulated heart signal to the pacer and for monitoring the electrical signals from the pacer;
a heart stimulating circuit having adjustable operating parameters for pacing said heart;
control means for manually selecting one of a plurality of electrical signals of the heart and pacer to be monitored and for manually selecting and adjusting the operating parameters of said pacer operating and heart stimulating circuits;
said control means including a single moveable adjustment means for selecting the value of each operating parameter from a predetermined range of selectable values;
enabling processing means, including a first microprocessor, for activating said heart stimulating circuit to pace the heart;
said enabling processing means further including multiplexing means for selectively transmitting values representing the electrical signals monitored by the sensing and pacer operating circuits;
supervised processing means, including:
a second microprocessor for generating the value of each operating parameter and for modifying said value by a predetermined increment in response to movement of the adjustment means, said value, increment and range determined by the selected operating parameter;
means for controlling the selection of values by the multiplexing means, and for receiving said selected values;
means responsive to said enabling processing means, for applying the generated values of said operating parameters to said enabling processing means to control the operation of said heart stimulating circuit; and
memory means for storing said generated values of said operational parameters; and
display means, responsive to said supervising processing means, for displaying the generated values of the operating parameters and the received values selected by said multiplexing means.

31. The analyzer apparatus of claim 30 wherein the control means further includes a plurality of pushbutton switches each for generating a code indicating its activation to the supervising processing means.

32. The analyzer apparatus of claim 31 wherein the control means includes:
a plurality of indicator lamps; and
said enabling processing means includes means, responsive to the activation of said switches, for selectively illuminating said lamps to provide visual feedback of said activation.

33. The analyzer apparatus of claim 30 wherein said enabling processing means further includes output expanding means for generating control signals to selectively activate the sensing circuit or heart stimulating circuit.

34. The analyzer apparatus of claim 30 wherein the heart stimulating circuit includes an atrial stimulation circuit and a ventricular stimulation circuit, each responsive to said enabling processing means, for respectively selectively stimulating the atrium or ventricle of the heart.

35. The analyzer apparatus of claim 30 wherein the sensing circuit includes:
average current measuring means for generating a signal proportional to the average current generated by said heart stimulating circuit; and
filter means, having a predetermined frequency range, for transmitting a signal proportional to the monitored electrical signals from the heart when the frequency of said monitored signals is within said frequency range and for rejecting said monitored signals when the frequency of said signals is outside of said frequency range.

36. The analyzer apparatus of claim 35 wherein said filter means is a bandpass filter having a frequency range substantially similar to the frequency range of said pacer.

37. The analyzer apparatus of claim 30 wherein said memory means includes a random access memory and a read only memory.

38. The analyzer apparatus of claim 30 wherein said pacer operating circuit includes:
havesine generating means for generating the simulated heart signal having a haversine waveform;
signal output indicator means for indicating the presence of said electrical signals from the pacer; and
a peak indicator circuit for generating a signal proportional to the peak voltage of said electrical signals from the pacer.

39. The analyzer apparatus of claim 38 wherein said haversine generating means comprises:
a reference signal generator for producing a fixed reference signal;
a first multiplying digital-to-analog converter connected to the output of said reference signal generator and responsive to the supervising processing means for generating a variable reference signal, said variable reference signal being a multiple of the fixed reference signal;
a second multiplying digital-to-analog converter, responsive to the supervising processing means, for producing a haversine signal of varying rate, said second digital-to-analog converter, responsive to said variable reference signal, for varying the amplitude of said haversine signal.

40. The analyzer apparatus of claim 38 wherein the signal output indicator means is a Schmitt trigger.

41. An analyzer apparatus, having a plurality of operating states, connected to a heart and an implantable pacer for monitoring the operation of the heart and the pacer and for testing the pacing operation of the pacer, the apparatus comprising:
circuit means, having a plurality of adjustable operating parameters, for stimulating the heart and pacer and for monitoring the electrical impulses of the heart and pacer;
control means including manually activated mode selection means, command selection means, and programmable function selection means for selecting the operating state of the analyzer;
the control means including a single moveable adjustment means for choosing the value of each adjustable operating parameter;
processing means, responsive to said control means, for generating first signals representative of the chosen value of each adjustable operating parameter and applying said first signals to said circuit means, for controlling the operation of said circuit means, and, responsive to said circuit means, for generating second signals representative of the electrical impulses of the heart and pacer; and
display means, responsive to said processing means, for displaying said first and second signals.

42. The analyzer apparatus of claim 41 wherein said processing means includes:
a first microprocessor for computing the values of said first and second signals; and
a second microprocessor for activating the circuit means at intervals determined by said first signals and said electrical impulses.

43. In the analyzer apparatus of claim 42:
said circuit means includes multiplier means, responsive to said first signals, for generating output signals to said heart and pacer; and
said first microprocessor includes programming means for converting the chosen value of each adjustable operating parameter into multiplier values,
and means for applying said multiplier values to said multiplier means so that the output signals are equal to the chosen value of each adjustable operating parameter.

44. The analyzer apparatus of claim 43 wherein said multiplier means includes a plurality of digital-to-analog converters.

45. The analyzer apparatus of claim 43 wherein said circuit means further includes a plurality of means, responsive to said processing means, for converting the electrical impulses of the heart and pacer into signals representing the operating characteristics of said heart and pacer.

* * * * *